(12) United States Patent  (10) Patent No.: US 11,969,144 B2
Uyama et al.  (45) Date of Patent: Apr. 30, 2024

(54) MEDICAL OBSERVATION SYSTEM, MEDICAL OBSERVATION APPARATUS AND MEDICAL OBSERVATION METHOD

(71) Applicant: Sony Corporation, Tokyo (JP)

(72) Inventors: Keisuke Uyama, Tokyo (JP); Tsuneo Hayashi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 616 days.

(21) Appl. No.: 17/263,557

(22) PCT Filed: Sep. 5, 2019

(86) PCT No.: PCT/JP2019/034929
§ 371 (c)(1),
(2) Date: Jan. 27, 2021

(87) PCT Pub. No.: WO2020/054566
PCT Pub. Date: Mar. 19, 2020

(65) Prior Publication Data
US 2021/0244260 A1  Aug. 12, 2021

(30) Foreign Application Priority Data
Sep. 11, 2018 (JP) .................................. 2018-169877

(51) Int. Cl.
A61B 1/00 (2006.01)
A61B 90/00 (2016.01)
A61B 90/25 (2016.01)

(52) U.S. Cl.
CPC .... *A61B 1/000094* (2022.02); *A61B 1/00048* (2013.01); *A61B 1/0005* (2013.01);
(Continued)

(58) Field of Classification Search
CPC ................ A61B 1/00048; A61B 90/25; A61B 1/000094
See application file for complete search history.

(56) References Cited

U.S. PATENT DOCUMENTS 6,414,708 B1  7/2002  Carmeli
11,730,562 B2 * 8/2023  Komp .............. A61B 1/000094
                                                    348/45
(Continued)

FOREIGN PATENT DOCUMENTS

CN   101677837 A   3/2010
CN   103251455 A   8/2013
(Continued)

OTHER PUBLICATIONS

International Search Report and Written Opinion dated Dec. 3, 2019, received for PCT Application PCT/JP2019/034929, Filed on Sep. 5, 2019, 8 pages including English Translation.

*Primary Examiner* — John P Leubecker
*Assistant Examiner* — Jae Woo
(74) *Attorney, Agent, or Firm* — XSENSUS LLP

(57) ABSTRACT

A three-dimensional information generation unit generates a three-dimensional map (D(X, Y, Z)) (three-dimensional information) regarding a surgical field, based on a surgical field image (K(x, y)) captured by an imaging device. A region-of-interest setting unit (setting unit) then sets at least one region-of-interest in the surgical field image (K(x, y)) captured at a predetermined timing. Based on the three-dimensional map (D(X, Y, Z)) and the position of the region-of-interest set by the region-of-interest setting unit, a region-of-interest estimation unit (estimation unit) estimates an existence position of the region-of-interest from within the surgical field image (K(x, y)) captured at a timing different from the predetermined timing. Subsequently, a zoom processing unit (magnified image generation unit) generates a magnified surgical field image (L(x, y)) in which the estimated region-of-interest is magnified by a predetermined magnification, and a display control unit outputs at least the magnified surgical field image (L(x, y)).

20 Claims, 21 Drawing Sheets

(52) U.S. Cl.
CPC ...... *A61B 1/00188* (2013.01); *A61B 1/00194*
(2022.02); *A61B 90/25* (2016.02); *A61B 90/36*
(2016.02); *A61B 2090/367* (2016.02)

(56) References Cited

U.S. PATENT DOCUMENTS

| | | | |
|---|---|---|---|
| 2003/0151661 A1* | 8/2003 | Davidson | A61B 1/00045 |
| | | | 348/65 |
| 2012/0230898 A1 | 9/2012 | Yamaura | |
| 2017/0035268 A1* | 2/2017 | Kumar | G06T 7/507 |
| 2017/0046842 A1* | 2/2017 | Yamaguchi | G06T 7/0012 |
| 2017/0208252 A1* | 7/2017 | Tamura | A61B 1/05 |
| 2019/0114738 A1* | 4/2019 | Sonoda | A61B 1/000094 |

FOREIGN PATENT DOCUMENTS

| | | |
|---|---|---|
| CN | 106413510 A | 2/2017 |
| EP | 3151720 A | 4/2017 |
| JP | 5-337077 A | 12/1993 |
| JP | 2000330031 A | 11/2000 |
| JP | 2010-172673 A | 8/2010 |
| JP | 2011177635 A | 9/2011 |
| JP | 2015-228954 A | 12/2015 |
| JP | 2016-192986 A | 11/2016 |
| WO | 2017/057574 A1 | 4/2017 |
| WO | 2017/216922 A1 | 12/2017 |

\* cited by examiner

FIG.3
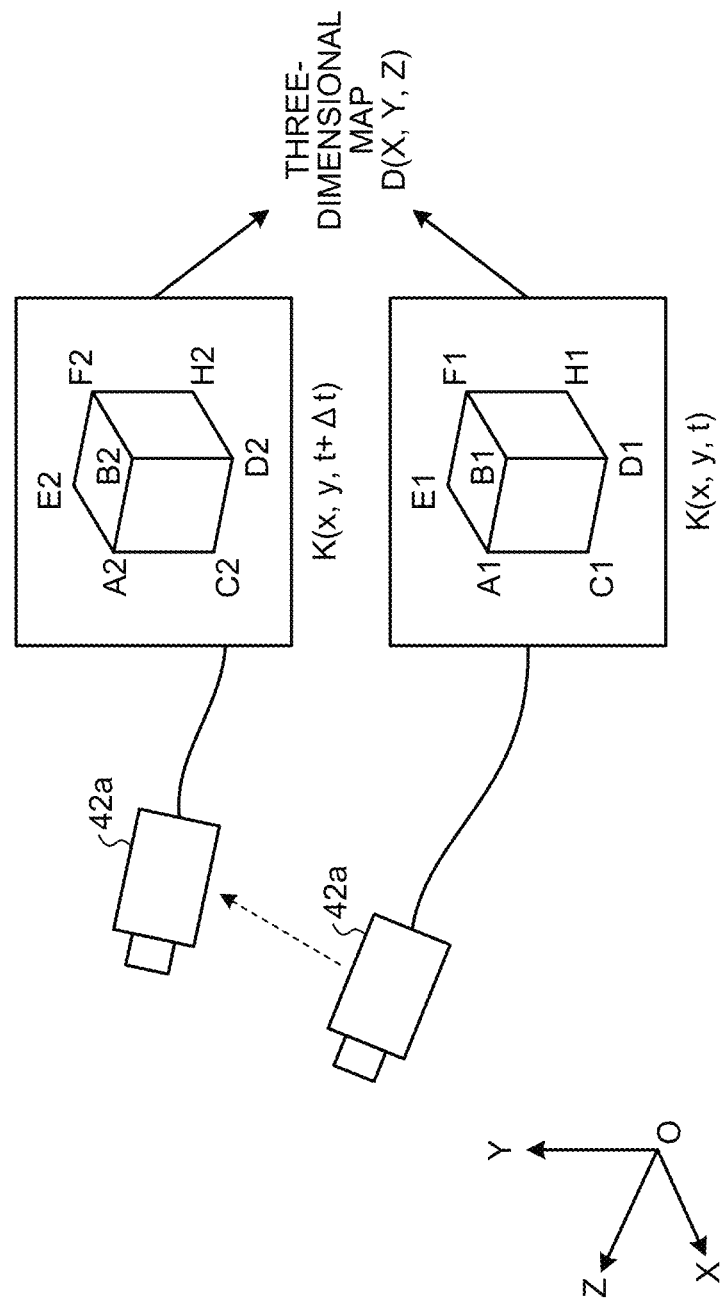
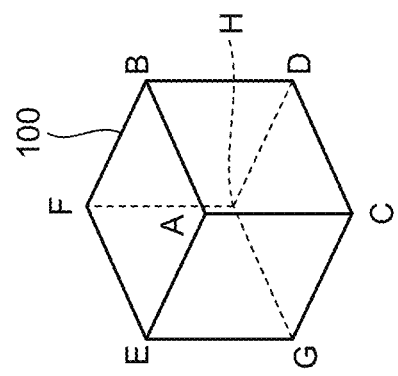

FIG.4
MOVE ENDOSCOPE SO THAT REGION DESIRED TO BE MAGNIFIED APPEARS IN CENTER
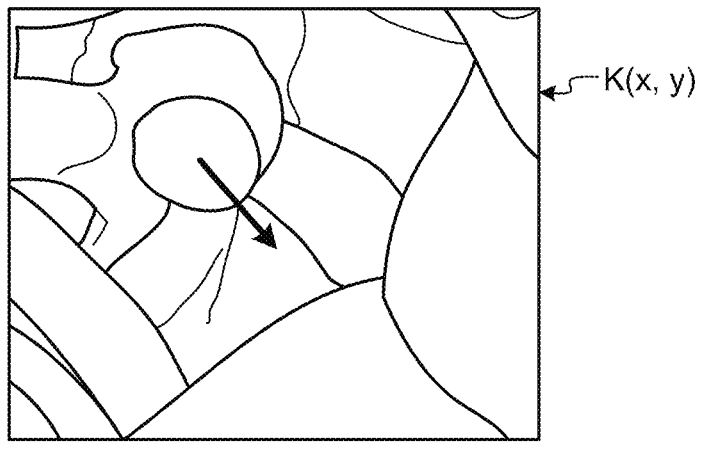
A
↓
AFTER CONFIRMING THAT REGION DESIRED TO BE MAGNIFIED APPEARS IN CENTER OF SCREEN, STEP ON FOOT SWITCH TO SET REGION-OF-INTEREST
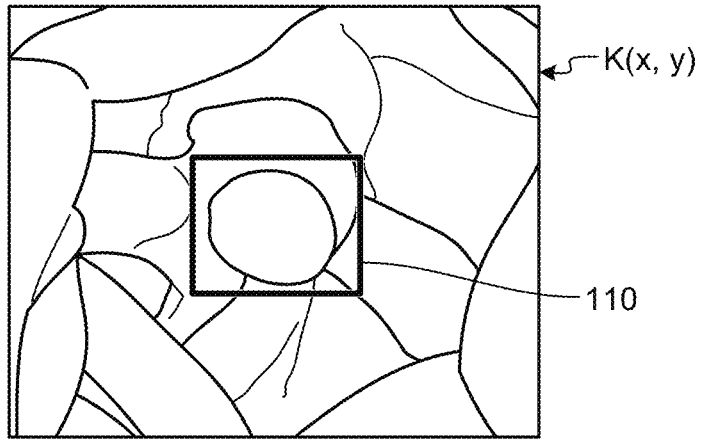
B
↓
CCU CONTROLS TO DISPLAY REGION INCLUDING REGION-OF-INTEREST IN MAGNIFIED STATE
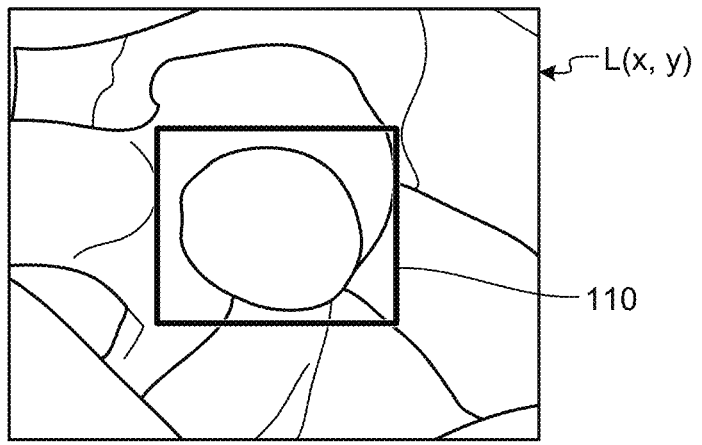
C FIG.5
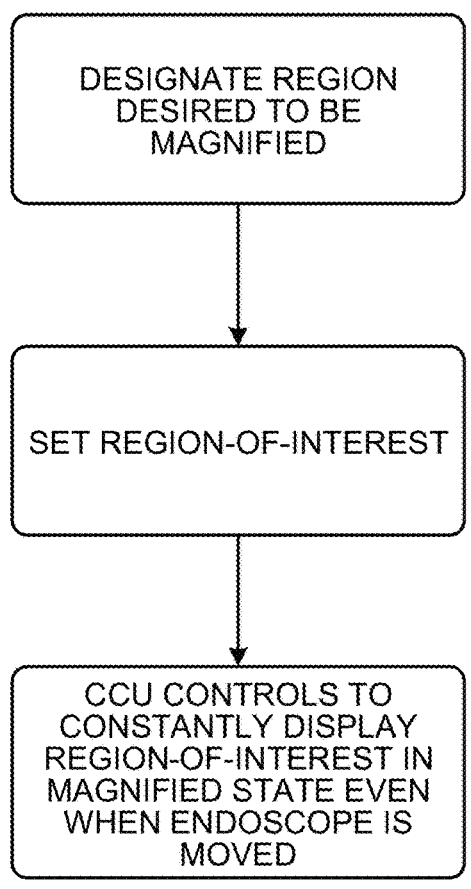
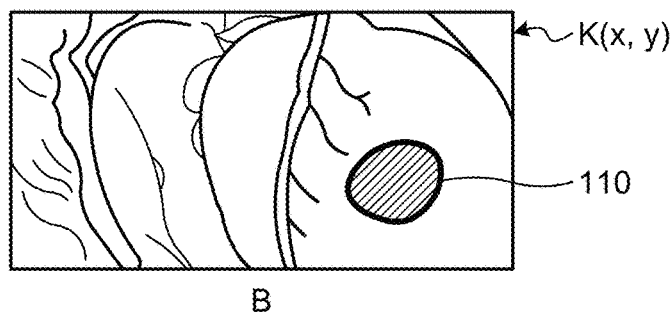
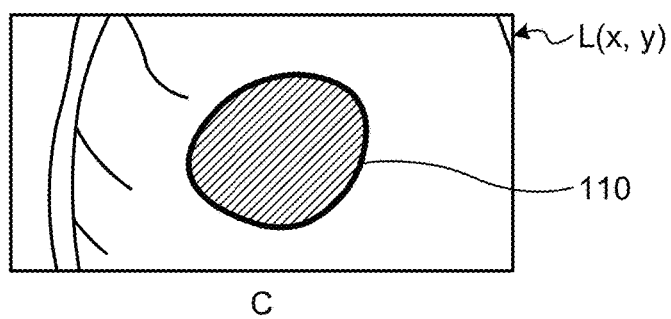

FIG.9
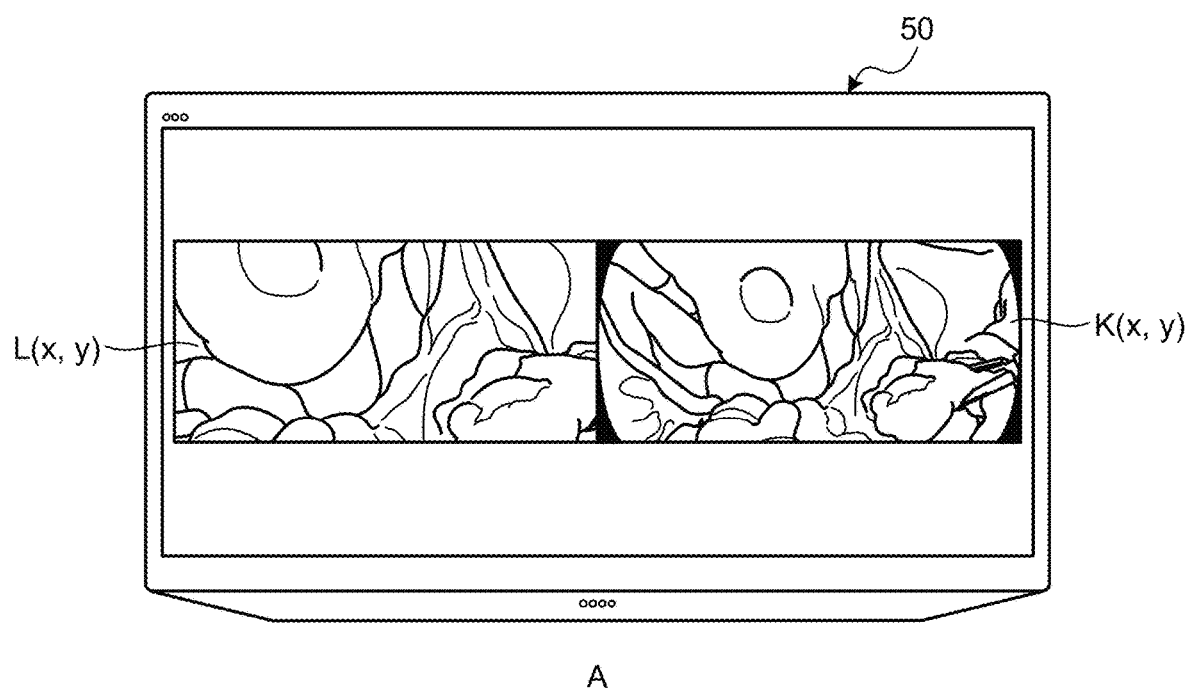
A
B

MEDICAL OBSERVATION SYSTEM, MEDICAL OBSERVATION APPARATUS AND MEDICAL OBSERVATION METHOD

CROSS-REFERENCE TO RELATED APPLICATIONS

The present application is based on PCT filing PCT/JP2019/034929, filed Sep. 5, 2019, which claims priority to JP 2018-169877, filed Sep. 11, 2018, the entire contents of each are incorporated herein by reference.

FIELD

The present disclosure relates to a medical observation system, a medical observation apparatus, and a medical observation method.

BACKGROUND

In recent years, there have been the increasing number of cases of performing surgeries using a medical observation apparatus such as a surgical endoscope or a surgical microscope in a state where a surgical field image is displayed on a large-screen display device and a surgeon performs the surgery while monitoring the surgical field image. The endoscope is used in a state of being inserted into the body. Therefore, the lens of the endoscope is affected by bleeding from inner portions of the body, scattering of smoke or oil due to the use of an energy device for tissue incision and detachment, or blood vessel seal with high-frequency current, ultrasonic vibration, or the like, resulting in attachment of stains and occurrence of fogging on the lens. Therefore, it has been necessary to frequently remove the endoscope and clean the lens. Therefore, in order to suppress stains and fogging on the lens, there is a proposed technique in which the surgical field of view (surgical field) is magnified and observed from a distant position, as illustrated in Patent Literature 1, for example.

CITATION LIST

Patent Literature

Patent Literature 1: JP 2016-192986 A

SUMMARY

Technical Problem

The technique disclosed in Patent Literature 1, however, uses a feature point and electronic zoom tracking is performed onto that position. Therefore, in a surgical operation, for example, in a case where an endoscope inserted into a body cavity is frequently moved in various directions for observation during the operation, an image captured by the endoscope involves a large movement, leading to insufficient tracking performance for the feature point. In addition, a treatment applied to the target tissue would change the appearance of that part, which causes a problem of making it difficult to track the feature point. This leads to a difficulty in achieving stable observation of the region to be magnified.

In view of this problem, the present disclosure proposes a medical observation system, a medical observation apparatus, and a medical observation method capable of magnifying and stably observing the affected part from a distant position.

Solution to Problem

To solve the problem described above, a medical observation system includes: an imaging device that images a surgical field and obtains a surgical field image; a three-dimensional information generation unit that generates three-dimensional information of the surgical field from the surgical field image captured by the imaging device; a setting unit that sets at least one region-of-interest within at least one the surgical field image captured at a predetermined timing by the imaging device; an estimation unit that estimates an existence position of the region-of-interest from within a surgical field image captured at a timing different from the predetermined timing based on the three-dimensional information and the position of the region-of-interest set by the setting unit; a magnified image generation unit that generates a magnified surgical field image in which the estimated region-of-interest is magnified at a predetermined magnification; and a display control unit that outputs at least the magnified surgical field image.

BRIEF DESCRIPTION OF DRAWINGS

FIG. 3 is a diagram illustrating an example of a method in which a map generation unit generates a three-dimensional map of a surgical field.

FIG. 4 is a diagram illustrating an example of a method of setting a region-of-interest frame.

FIG. 5 is a diagram illustrating another example of a method of setting a region-of-interest frame.

FIG. 9 is a view illustrating an example of a display mode of an image output by a display control unit to a display device.

DESCRIPTION OF EMBODIMENTS

Embodiments of the present disclosure will be described below in detail with reference to the drawings. In each of the following embodiments, the same parts are denoted by the same reference symbols, and a repetitive description thereof will be omitted.

First Embodiment

[Configuration of medical observation system according to first embodiment]

Figure 1:
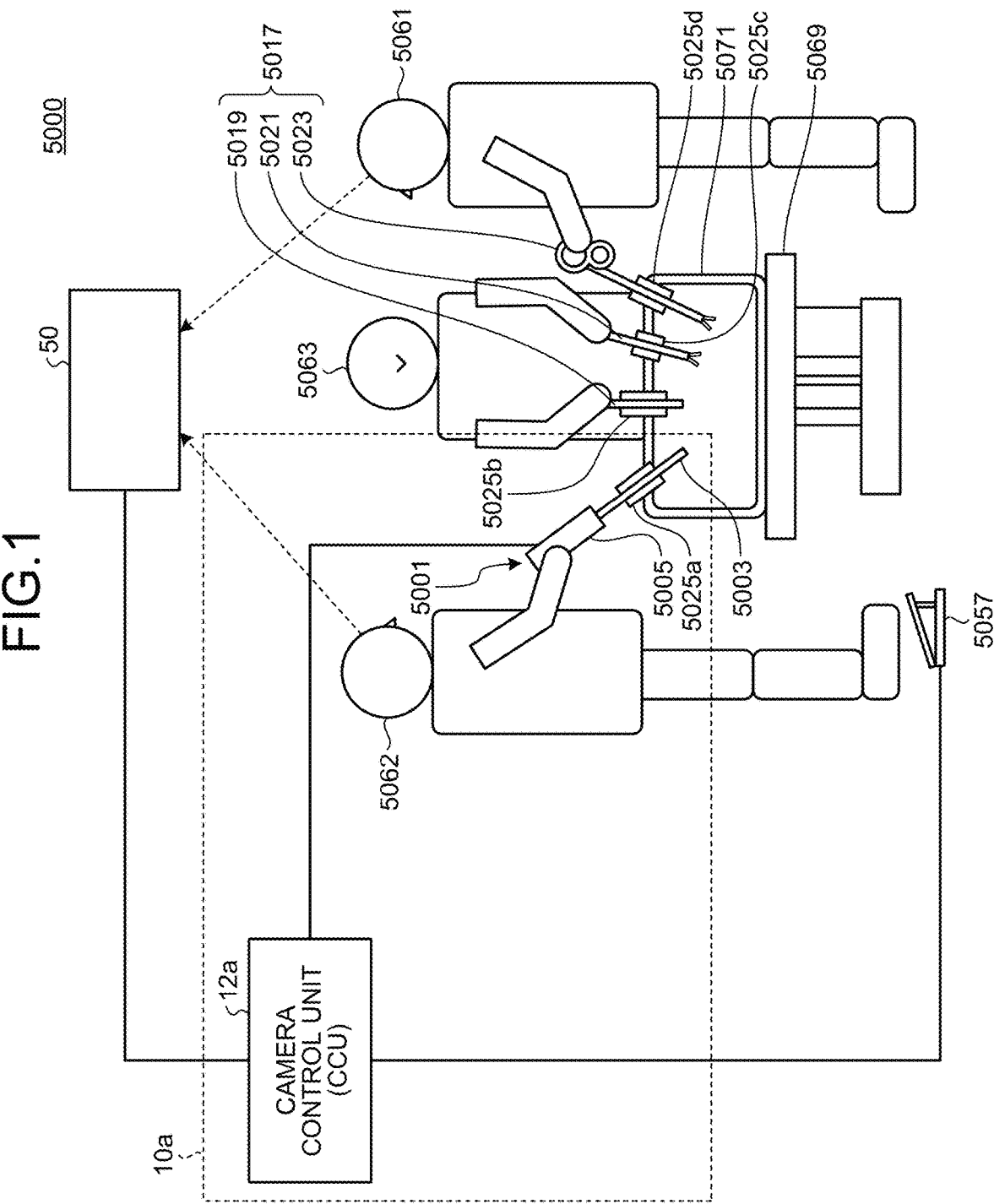
FIG. 1 is a view illustrating an example of a schematic configuration of an endoscopic surgery system to which a medical observation system according to a first embodiment of the present disclosure is applicable.

FIG. 1 is a view illustrating an example of a schematic configuration of an endoscopic surgery system 5000 to which a medical observation system according to the present disclosure is applicable. FIG. 1 illustrates a scene in which a surgeon (doctor) 5061 is during surgery on a patient 5071 on a patient bed 5069 using the endoscopic surgery system 5000. An endoscope operator 5062 holds an endoscope 5001 and inserts the endoscope 5001 into the body cavity of the patient 5071. An assistant 5063 is holding a surgical tool 5017 and inserting the tool into the body cavity of the patient 5071.

In endoscopic surgery, a plurality of tubular laparotomy instruments referred to as trocars 5025a to 5025d are punctured into an abdominal wall, instead of performing open surgery of cutting the abdominal wall. Through the trocars 5025a to 5025d, a lens barrel 5003 of the endoscope 5001 and other surgical tools 5017 are inserted into the body cavity of the patient 5071. In the example of FIG. 1, as other surgical tools 5017, an insufflation tube 5019, an energy treatment tool 5021 and forceps 5023 are being inserted into the body cavity of the patient 5071. The insufflation tube 5019 pumps gas into the body cavity of the patient 5071 to inflate the body cavity for the purpose of assuring the field of view for the endoscope 5001 and the work space for the surgeon 5061. The energy treatment tool 5021 is a treatment tool used for incision and detachment of tissues, blood vessel sealing, or the like, by using high-frequency current or ultrasonic vibration. Furthermore, although not illustrated in FIG. 1, the insufflation tube 5019 and the energy treatment tool 5021 are connected to a control device (not illustrated), and the surgical tool 5017 is used to perform predetermined operations, instructed by the surgeon 5061 or the like. The surgical tool 5017 illustrated in the figure is just an example, and other applicable examples of the surgical tool 5017 include various surgical tools generally used in endoscopic surgery, such as tweezers and a retractor.

An image of the surgical field in the body cavity of the patient 5071 (hereinafter referred to as a surgical field image) captured by the endoscope 5001 is displayed on a display device 50. While viewing the surgical field image displayed on the display device 50 in real time, the surgeon 5061 performs procedures such as resecting the affected part by using the energy treatment tool 5021 and the forceps 5023. In addition, the endoscope operator 5062 adjusts the position of the endoscope 5001 while viewing the surgical field image displayed on the display device 50 in real time so that the affected part is positioned within the surgical field image. The insufflation tube 5019, the energy treatment tool 5021, and the forceps 5023 are held by the surgeon 5061, the assistant 5063, or the like during the surgery.

Schematic Configuration of Endoscope

The endoscope 5001 includes: a lens barrel 5003 (also referred to as a scope), a region of a predetermined length from a distal end of which is inserted into the body cavity of the patient 5071; and a camera head 5005 connected to a proximal end of the lens barrel 5003. The example of FIG. 1 illustrates the endoscope 5001 as a rigid scope having the lens barrel 5003 of a rigid type. However, the endoscope 5001 can be a flexible scope having the lens barrel 5003 of a flexible material.

The distal end of the lens barrel 5003 has an aperture to which an objective lens is fitted. The endoscope 5001 is connected to a light source device (not illustrated). The light generated by the light source device is guided to the distal end of the lens barrel 5003 by a light guide extending inside the lens barrel 5003, and this guided light will be emitted toward an observation target in the body cavity of the patient 5071 through the objective lens. The endoscope 5001 may be a forward viewing endoscope, a forward-oblique viewing endoscope, or a side-viewing endoscope.

An optical system and an imaging element are provided inside the camera head 5005. Reflected light (observation light) from the observation target is focused onto the imaging element by the optical system. The observation light is photoelectrically converted by the imaging element so as to generate an electric signal corresponding to the observation light, that is, an image signal corresponding to the observation image. The image signal is transmitted as RAW data to a camera control unit (CCU) 12a. The camera head 5005 has a function of adjusting a magnification and a focal length by appropriately driving the optical system.

Furthermore, the camera head 5005 may include a plurality of imaging elements in order to support stereoscopic viewing (3D display) or the like. In this case, a plurality of relay optical systems is provided inside the lens barrel 5003 in order to guide the observation light to each of the plurality of imaging elements.

The endoscopic surgery system 5000 includes an input device that receives various information inputs and instruction inputs from the user, namely, the surgeon 5061, the endoscope operator 5062, or the assistant 5063. For example, the user inputs various types of information related to the surgery, such as physical information regarding the patient and information regarding the surgical procedure, via the input device. Furthermore, the user inputs, through the input device, an instruction to change imaging conditions (type of irradiation light, magnification, focal length, or the like) of the endoscope 5001, an instruction to drive the surgical tool 5017 such as the energy treatment tool 5021, for example.

The type of input device is not limited, and the input device may be various known input devices. Examples of applicable input devices include a mouse, a keyboard, a touch panel, a switch and/or a lever. FIG. 1 illustrates an example in which an endoscope operator 5062 inputs information using a foot switch 5057, which is an example of the input device. For example, the endoscope operator 5062 sets a region-of-interest in a surgical field image via the foot switch 5057. Details of this will be described below. When a touch panel is used as an input device, the touch panel may be provided on a display surface of the display device 50.

[Configuration of Medical Observation System According to First Embodiment]

Figure 2:
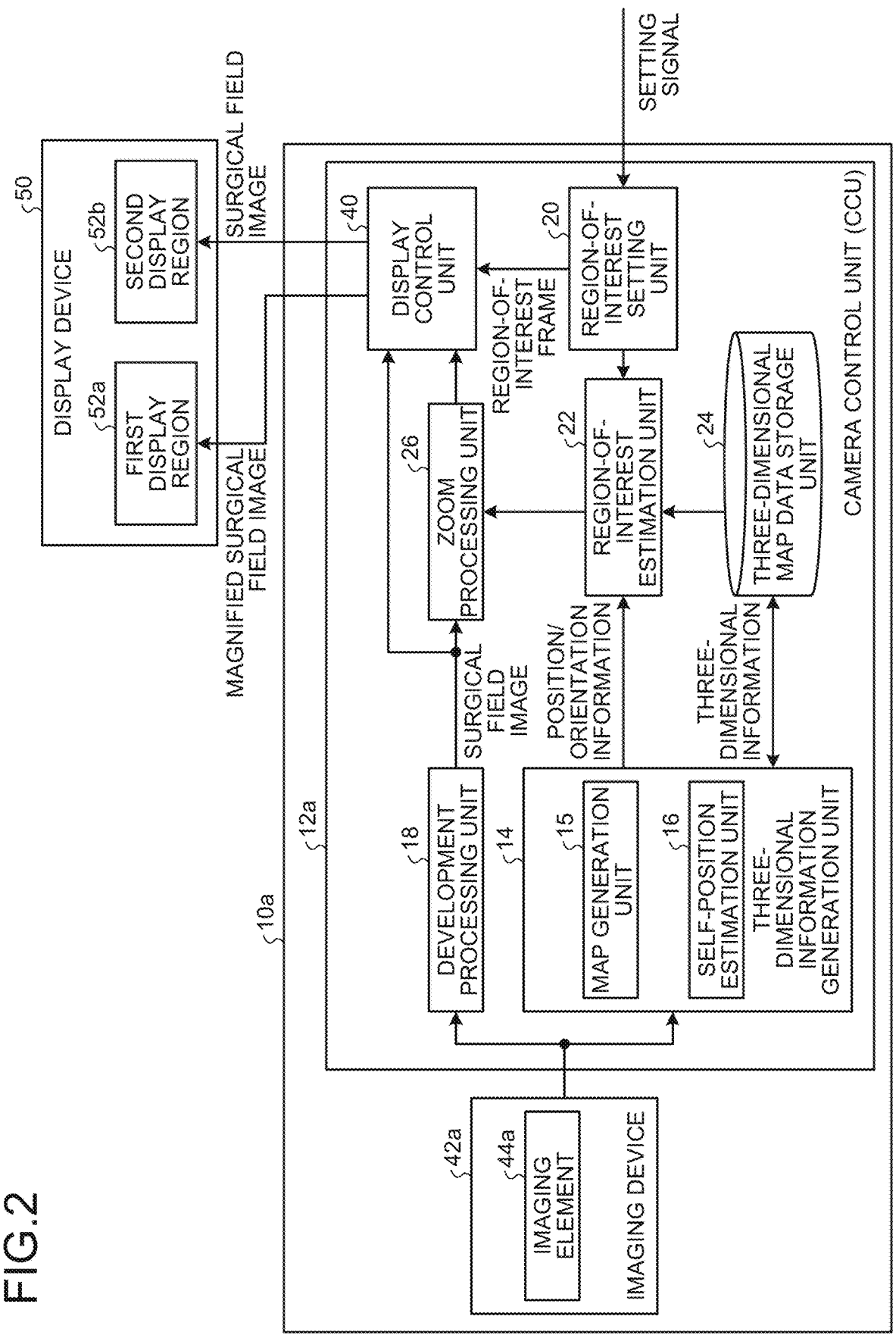
FIG. 2 is a diagram illustrating an example of a schematic configuration of a medical observation system according to the first embodiment of the present disclosure.

FIG. 2 is a functional block diagram illustrating a functional configuration of a medical observation system 10*a* applicable to endoscopic surgery. The medical observation system 10*a* is a system applied to the endoscopic surgery system 5000 described above and configured to monitor a surgical field image by the endoscope 5001 inserted into the body cavity of the patient 5071 during surgery. In particular, the medical observation system 10*a* is a system that constantly displays a magnified surgical field image obtained by magnifying the set region-of-interest based on a three-dimensional position of the surgical field, regardless of the position and orientation of the endoscope 5001.

The medical observation system 10*a* includes an imaging device 42*a* and a camera control unit 12*a*. Mounted on the camera head 5005 of the endoscope 5001 described above, the imaging device 42*a* images the surgical field in the body cavity of the patient 5071 to obtain a surgical field image. When the imaging device 42*a* captures an image, the camera control unit 12*a* generates a surgical field image as well as generating three-dimensional information regarding the surgical field.

The imaging device 42*a* includes an imaging element 44*a*. The imaging element 44*a* is represented by an imaging element (photoelectric conversion element) such as a complementary metal oxide semiconductor (CMOS) image sensor or a charge coupled device (CCD) image sensor, and converts light from the surgical field into an electric signal.

The camera control unit 12*a* includes a three-dimensional information generation unit 14, a development processing unit 18, a region-of-interest setting unit 20, a region-of-interest estimation unit 22, a three-dimensional map data storage unit 24, a zoom processing unit 26, and a display control unit 40. The camera control unit 12*a* constantly generates a magnified surgical field image in which the region-of-interest is magnified regardless of the position and orientation of the endoscope, and displays the generated image on the display device 50. The camera control unit 12*a* is an example of the medical observation apparatus in the present disclosure.

The three-dimensional information generation unit 14 calculates a three-dimensional position of the surgical field image in the body cavity captured by the imaging element 44*a*, for example. The three-dimensional information generation unit 14 includes a map generation unit 15 and a self-position estimation unit 16. The map generation unit 15 generates a three-dimensional map (hereinafter, simply referred to as a map) indicating a three-dimensional position of the surgical field and a three-dimensional position of the region-of-interest described below. A method for generating a map will be described below. The self-position estimation unit 16 estimates the self-position and orientation of the endoscope 5001 at a predetermined timing based on the generated map and the surgical field image captured at the predetermined timing.

The development processing unit 18 performs development processing of converting the captured data into a visible image. The development processing unit 18 applies various image processing for displaying an image, such as development processing (demosaic processing), on RAW data output by the imaging element 44*a*. More specifically, the development processing unit 18 converts the RAW data into visible image data by applying a preset digital gain or gamma curve to the RAW data. It is desirable to preliminarily adjust the digital gain and gamma curve to set in order to be able to generate image data having high visibility for the surgeon 5061 and the endoscope operator 5062.

The region-of-interest setting unit 20 designate a region-of-interest, such as a tumor to be removed by surgery, from within the surgical field image captured by the imaging element 44*a* and converted into a visible image by the development processing unit 18. More specifically, a manipulator of the medical observation system 10*a* sets at least one region-of-interest from within the surgical field image while monitoring the surgical field image on the display device 50 such as a liquid crystal monitor. A specific method of setting the region-of-interest will be described below. The region-of-interest setting unit 20 is an example of a setting unit in the present disclosure.

The region-of-interest estimation unit 22 estimates an existence position of the region-of-interest in the surgical field image at a certain timing. The region-of-interest estimation unit 22 is an example of an estimation unit in the present disclosure.

The three-dimensional map data storage unit 24 stores the three-dimensional map of the surgical field generated by the map generation unit 15 described above. The three-dimensional map stored in the three-dimensional map data storage unit 24 is updated with the passage of time.

The zoom processing unit 26 generates a magnified surgical field image obtained by magnifying the region-of-interest estimated at the timing, based on the existence position of the region-of-interest estimated by the region-of-interest estimation unit 22. The zoom processing unit 26 is an example of a magnified image generation unit in the present disclosure. The zoom processing unit 26 performs electronic zoom processing on the surgical field image by interpolating pixel values between pixels, for example, Pixel value interpolation may be performed by using a known method such as the nearest neighbor interpolation, the bilinear interpolation, the bicubic interpolation, or the Lanczos algorithm. Furthermore, the zoom processing unit 26 may perform electronic zooming by additionally using super-resolution processing.

The zoom magnification may be a predetermined magnification set in advance, or may be automatically determined by the zoom processing unit 26 based on the size of the region-of-interest. Alternatively, a user such as the endoscope operator 5062, as a manipulator, may specify the magnification.

The display control unit 40 performs display control of outputting the surgical field image generated by the development processing unit 18 and the magnified surgical field image generated by the zoom processing unit 26 to the display device 50. Examples of the applicable display device 50 include various known display devices such as a liquid crystal display device or an electro luminescence (EL) display device. The display device 50 includes a first display region 52a in which at least a magnified surgical field image is to be displayed. Furthermore, as illustrated in FIG. 2, the display device 50 may include a second display region 52b in which the surgical field image is to be displayed, in addition to the first display region 52a. In that case, the display device 50 may include both the first display region 52a and the second display region 52b in one monitor. Alternatively, the display device 50 may be formed of two different monitors, each of which including the first display region 52a and the second display region 52b, individually.

[Method for Generating a Three-Dimensional Map]

Next, a method in which the map generation unit 15 generates a three-dimensional map of the surgical field will be described. FIG. 3 is a diagram illustrating a method in which the map generation unit 15 generates a three-dimensional map of the surgical field.

FIG. 3 illustrates a scene in which an object 100, which is a stationary object, is observed by the imaging device 42a in a three-dimensional space XYZ having a point in the space as a reference position O. This scene assume a case where the imaging device 42a captures a surgical field image K(x, y, t) at a predetermined timing, time t, for example, and captures a surgical field image K(x, y, t+Δt) at a timing different from the predetermined timing, for example, at time t+Δt. Note that a time interval Δt is set to 33 msec, for example. Furthermore, the reference position O may be set to any position, but is to be desirably set to a position that would not move with time, for example. Note that x in the surgical field image K(x, y, t) represents coordinates of the image in the horizontal direction, and y represents coordinates of the image in the vertical direction.

The map generation unit 15 first detects a feature point, which is a characteristic pixel, from within the surgical field image K(x, y, t) and the surgical field image K(x, y, t+Δt). An example of the feature point is a pixel having a pixel value different from the pixel values of adjacent pixels by a predetermined value or more. The feature point is desirably a point that exists stably even with a passage of time. For example, pixels forming an edge in an image are often used as the feature point. Here, in order to simplify the following description, it is assumed that feature points A1, B1, C1, D1, E1, F1, and H1, which are the vertices of the object 100, have been detected from within the surgical field image K(x, y, t).

Next, the map generation unit 15 searches the surgical field image K(x, y, t+Δt) for points corresponding to the feature points A1, B1, C1, D1, E1, F1, and H1, individually. Specifically, the map generation unit 15 searches the surgical field image K(x, y, t+Δt) for a point having the similar feature based on the pixel value of the feature point A1 and the pixel values in the vicinity of the feature point A1, or the like. By this search process, it is assumed that feature points A2, B2, C2, D2, E2, F2, and H2 have been detected corresponding to the feature points A1, B1, C1, D1, E1, F1, and H1 respectively, from within the surgical field image K(x, y, t+Δt).

Subsequently, based on the principle of three-dimensional surveying, the map generation unit 15 calculates three-dimensional coordinates $(X_A, Y_A, Z_A)$ of a point A in space using two-dimensional coordinates of the feature point A1 on the surgical field image K(x, y, t+Δt) and the two-dimensional coordinates of the feature point A2 on the surgical field image K(x, y, t+Δt). A three-dimensional map D(X, Y, Z) of the space in which the object 100 is located will be generated as a set of the three-dimensional coordinates $(X_A, Y_A, Z_A)$ calculated in this manner. The generated three-dimensional map D(X, Y, Z) is stored in the three-dimensional map data storage unit 24. The three-dimensional map D(X, Y, Z) is an example of three-dimensional information in the present disclosure.

Since the position and orientation of the imaging device 42a have changed during a time interval Δt, the map generation unit 15 also estimates the position and orientation of the imaging device 42a at the same time. Mathematically, based on the two-dimensional coordinates of the feature points individually observed on the surgical field image K(x, y, t) and the surgical field image K(x, y, t+Δt), simultaneous equations are formulated using the three-dimensional coordinates of individual feature points constituting the object 100 and the position and orientation of the imaging device 42a, as unknown quantities. By solving this set of simultaneous equations, the map generation unit 15 estimates the three-dimensional coordinates of the individual feature points constituting the object 100 as well as the position and orientation of the imaging device 42a.

In this manner, by detecting a plurality of feature points from within the surgical field image K(x, y, t) captured by the imaging device 42a, and detecting, from within the surgical field image K(x, y, t+Δt), points corresponding to those feature points, it is possible to generate a three-dimensional map D(X, Y, Z) of the environment observed by the imaging device 42a.

Furthermore, it is also possible to estimate the position and orientation, namely, the self-position, of the imaging device 42a. Furthermore, repeatedly executing the above-described processing, for example, makes it possible to visualize the feature points that have been invisible earlier, leading to expansion of the three-dimensional map D(X, Y, Z). Furthermore, repeated processing can lead to repeated calculation of the three-dimensional position of the same feature point. Accordingly, the calculation error can be reduced by performing averaging processing, for example. In this manner, the three-dimensional map D(X, Y, Z) stored in the three-dimensional map data storage unit 24 is updated as needed. The technology for creating a three-dimensional map of the environment as well as specifying the self-position of the imaging device 42a is generally called simultaneous localization and mapping (SLAM) technology.

The basic principles of SLAM technology using monocular cameras are described, for example, in "Andrew J. Davison, "Real-Time Simultaneous Localization and Mapping with a Single Camera", Proceedings of the 9th IEEE International Conference on Computer Vision Volume 2, 2003, pp. 1403-1410". The SLAM technology that estimates the three-dimensional position of a subject using a camera image of the subject is also referred to as Visual SLAM.

Method of Setting Region-of-Interest

A region-of-interest is set by the operation of the region-of-interest setting unit 20. Specifically, the region-of-interest setting unit 20 sets a region-of-interest by performing a display of a region-of-interest frame indicating a region-ofinterest so as to be superimposed on a surgical field image and designating the size, shape, and position of the region-of-interest frame.

FIG. 4 is a diagram illustrating an example of a method of setting the region-of-interest frame. FIG. 4A is a view illustrating an example of a surgical field image K(x, y) observed by the endoscope 5001. Hereinafter, information regarding the timing (for example, time) of capturing the surgical field image will be omitted, and the surgical field image will be simply described as K(x, y). FIG. 4b is a view illustrating an example of a state in which the orientation of the endoscope 5001 is adjusted so that the affected part desired to be set as the region-of-interest comes at the center of the surgical field image K(x, y), and the region-of-interest setting unit 20 has set a region-of-interest frame 110 indicating the region-of-interest. FIG. 4C is a view illustrating an example of a magnified surgical field image L(x, y) in which a region including the region-of-interest frame 110 is displayed in a state of being magnified at a predetermined magnification.

For example, while viewing the surgical field image K(x, y) illustrated in FIG. 4A, for example, the endoscope operator 5062 moves the endoscope 5001 so that the specific position desired to be magnified, such as the affected part, comes at the center (an example of a predetermined position) of the surgical field image K(x, Y).

As illustrated in FIG. 4B, when the specific position of interest appears in the center of the surgical field image K(x, y) (an example of a predetermined position), the endoscope operator 5062 steps on the foot switch 5057 (FIG. 1) to instruct the region-of-interest setting unit 20 to set the region-of-interest. At this time, triggered by stepping on the foot switch 5057, a setting signal instructing the setting of the region-of-interest is generated. On condition that the setting signal has been input, the region-of-interest setting unit 20 controls to display the region-of-interest frame 110 of a predetermined size at the center of the surgical field image K(x, y) as illustrated in FIG. 4B, thereby setting the region-of-interest. The size and shape of the region-of-interest frame 110 may be set flexibly, and details of which will be described below.

The region-of-interest setting method performed by the region-of-interest setting unit 20 is not limited to the above-described method. For example, a touch panel may be overlaid on the screen of the display device 50, and an operation on the touch panel may be detected to set a region-of-interest at a position where the touch panel has been operated. In addition, the position and shape of the region-of-interest may be set with a mouse. Furthermore, the region-of-interest setting unit 20 may set the position and shape of the region-of-interest based on an operation such as a gesture.

FIG. 5 is a diagram illustrating another example of the method of setting the region-of-interest frame. FIG. 5A is a view illustrating an example of a surgical field image K(x, y) observed by the endoscope 5001. The endoscope operator 5062 designates the position of the region-of-interest by using an input device such as a touch panel or a mouse while monitoring the surgical field image K(x, y) displayed on the display device 50. The region-of-interest setting unit 20 controls to display region-of-interest instruction information 105 indicating the designated region so as to be superimposed on the surgical field image K(x, y).

Subsequently, the region-of-interest setting unit 20 sets the region-of-interest frame 110 at the position of the input region-of-interest instruction information 105. The region-of-interest setting unit 20 controls to display the set region-of-interest frame 110 so as to be superimposed on the surgical field image K(x, y), as illustrated in FIG. 5B. The region-of-interest frame 110 may be a frame having a preset size and shape, or may be a closed region modeled upon the region-of-interest instruction information 105.

Thereafter, regardless of the position and orientation of the endoscope 5001, the zoom processing unit 26 generates a magnified surgical field image L(x, y) obtained by magnifying the set region-of-interest frame 110 by a predetermined magnification, and displays the generated image as illustrated in FIG. 5C.

In addition, the region-of-interest setting unit 20 may use the above-described three-dimensional map D(X, Y, Z) and may set the region-of-interest in consideration of conditions such that the distance in the three-dimensional space or the distance from the imaging system is within a certain range. Furthermore, the display mode of the region-of-interest frame 110 is not limited to that illustrated in FIGS. 4 and 5. The variation of the display mode of the region-of-interest frame 110 will be described below (refer to FIG. 18). Furthermore, the region-of-interest setting unit 20 may set the position and shape of the region-of-interest based on an operation such as a gesture.

Subsequently, as illustrated in FIG. 4C, the zoom processing unit 26 generates a magnified surgical field image L(x, y) obtained by magnifying the region including the region-of-interest frame 110 of the surgical field image K(x, y) by a predetermined magnification. At this time, as illustrated in FIG. 4C, the region-of-interest frame 110 is also displayed as an image magnified at a predetermined magnification. Subsequently, the display control unit 40 controls to output and display the generated magnified surgical field image L(x, y) to the display device 50. The surgeon 5061 performs an operation while observing the magnified surgical field image L(x, y) displayed on the display device 50.

Although not illustrated in FIG. 4, after generation of the magnified surgical field image L(x, y), the medical observation system 10a repeats imaging/display of the surgical field image K(x, y) at a predetermined time interval Δt. Every time the surgical field image K(x, y) is captured, the generation and display of a new magnified surgical field image L(x, y) will be repeated.

[Method of Estimating Existence Position of Region-of-Interest]

Thereafter, the position and orientation of the endoscope 5001 might change in some cases together with the passage of observation time for the surgical field image K(x, y). Subsequently, the region-of-interest estimation unit 22 estimates the existence position of the region-of-interest on the surgical field image K(x, y). The zoom processing unit 26 generates a magnified surgical field image L(x, y) in which the estimated region-of-interest is magnified by a predetermined magnification. As illustrated in FIG. 4C, the display control unit 40 controls to output and display the magnified surgical field image L(x, y) to the display device 50. By continuing such processing, the medical observation system 10a continues to display the magnified surgical field image L(x, y) on the display device 50.

Here, the following is a description of a method of estimating, by the region-of-interest estimation unit 22, the existence position of the region-of-interest from within the surgical field image K(x, y) in a case where the position or orientation of the endoscope 5001 has changed.

Based on the position and orientation of the endoscope 5001 at a predetermined timing, for example, at time t, the position and orientation of the endoscope 5001 at a timing different from the predetermined timing, for example, at time t+Δt, and the three-dimensional map D(X, Y, Z), the region-of-interest estimation unit 22 estimates a to-be-observed position of the region-of-interest frame 110 within the surgical field image K(x, y, t+Δt) at time t+Δt, which is currently at a present position at time t.

Specifically, based on the position and orientation of the endoscope 5001, the region-of-interest estimation unit 22 specifies how a plurality of feature points in the vicinity of the set region-of-interest frame 110 has moved during a period from time t and time t+Δt. Subsequently, the region-of-interest estimation unit 22 estimates the position of the region-of-interest based on the moving state of the specified feature point.

The region set as a region-of-interest is typically the affected part as a target of operation. The affected part is likely to be surgically resected, bleeding, or severely deformed. Therefore, even when a feature point is set within a region-of-interest, the feature point might disappear with the passage of time. Therefore, when extracting a feature point from the surgical field image K(x, y) to which the region-of-interest has been set, it is desirable to extract the feature point from within the regions excluding the neighboring region of the region-of-interest.

Figure 6:
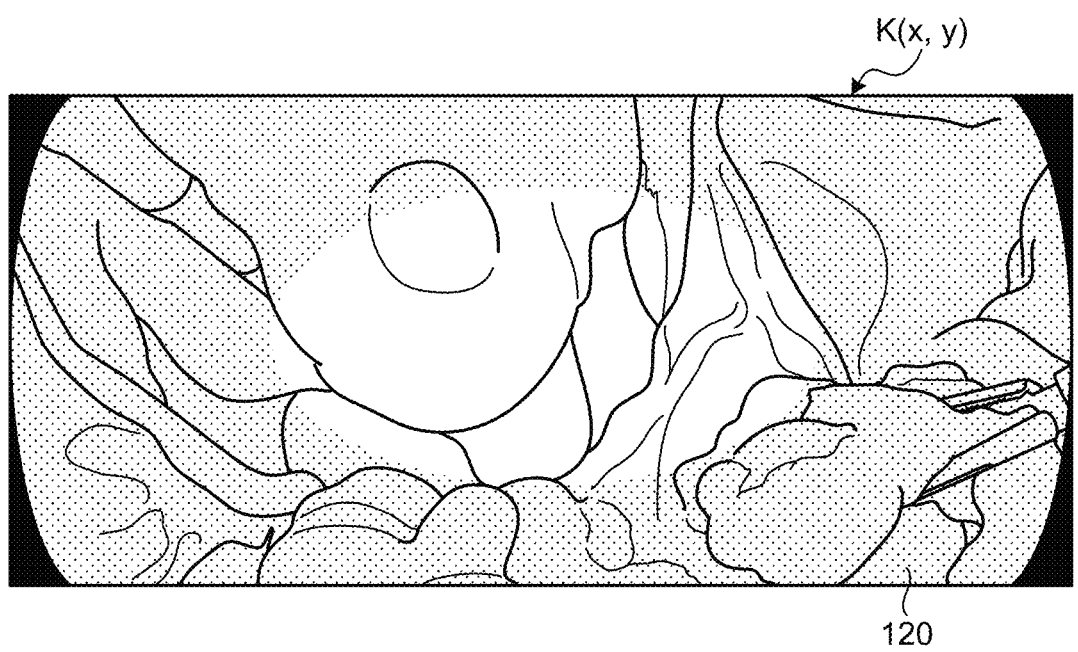
FIG. 6 is a diagram illustrating an example in which a feature point extraction region has been set.

FIG. 6 is an image illustrating an example in which a feature point extraction region has been set. As illustrated in FIG. 6, the above-described map generation unit 15 sets a mask 120 at the periphery of the screen, avoiding the central portion of the screen on which the region-of-interest frame 110 has been set. The map generation unit 15 extracts a feature point only inside the set mask 120. The region of the mask 120 that has been set is distant from the region-of-interest frame 110 indicating the position of the region-of-interest, and thus is not likely to have a large deformation during an operation. Accordingly, it is possible, at inside portions of the mask 120, to stably detect feature points regardless of the passage of time. Since the feature points can be extracted stably, it is possible to enhance the stability of accuracy in estimating the three-dimensional map D(X, Y, Z) and the position and orientation of the endoscope 5001.

Incidentally, there is a case where images of objects unrelated to the surgical field, such as a surgical instrument including forceps 5023 or operator's fingers, are captured inside the mask 120 in the surgical field image K(x, y). The feature points that make up these objects are likely to move irregularly over time. That is, there is no guarantee that these feature points exist stably in the surgical field image K(x, y), and thus, it is desirable to extract the feature points after removing these objects. For this purpose, the map generation unit 15 may have a function of removing objects such as surgical instruments and fingers registered in advance from the surgical field image K(x, y). This removal function is, for example, a function of performing image recognition for a pre-registered object and excluding the region in which the recognized object exists, from calculation.

[Image Displayed by Medical Observation System According to First Embodiment]

Figure 7:
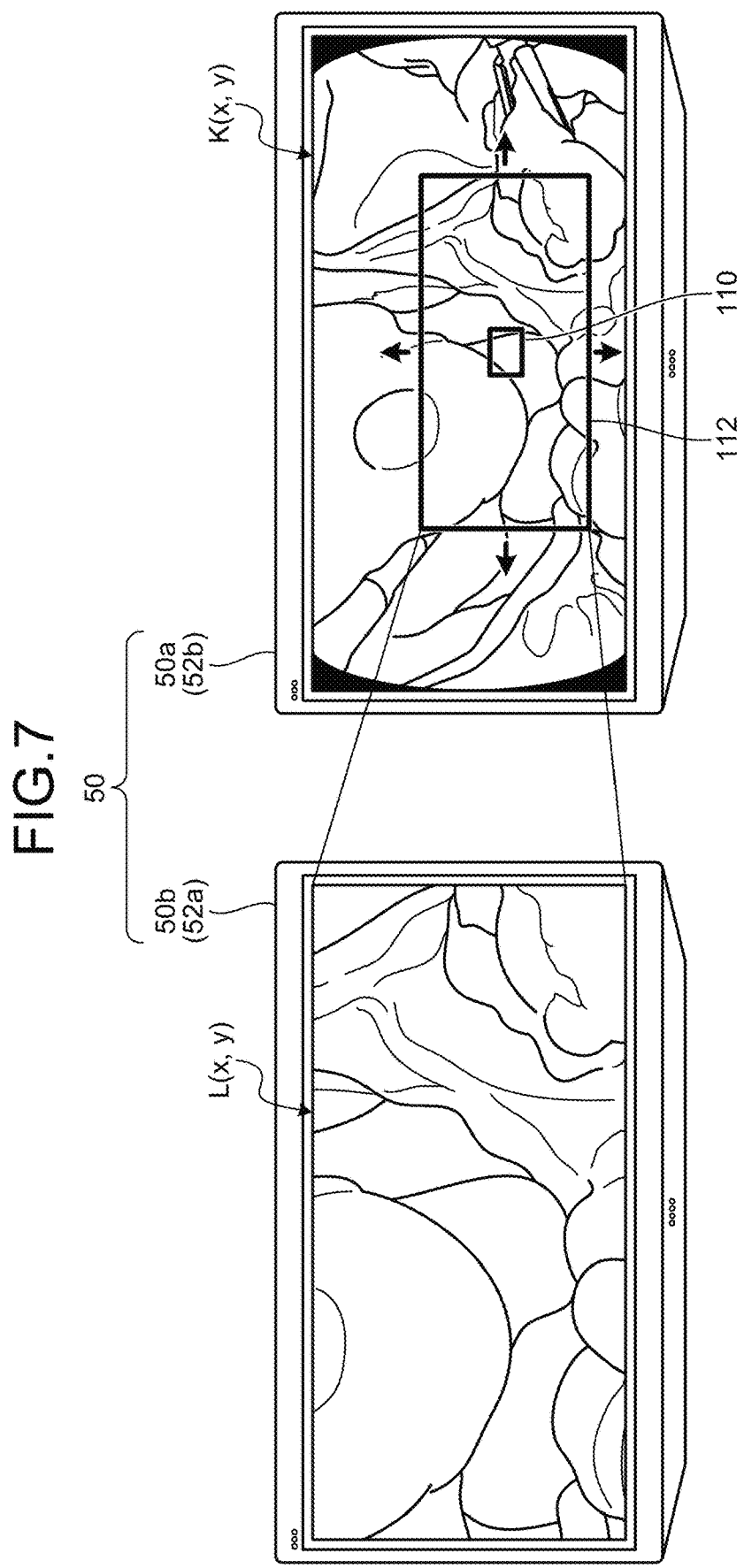
FIG. 7 is a view illustrating an example of an image displayed by a medical observation system.

FIG. 7 is a view illustrating an example of an image displayed by the medical observation system 10a. As illustrated in FIG. 7, the display control unit 40 controls to output and display the surgical field image K(x, y) monitored by the endoscope operator 5062 to a display device 50a (the second display region 52b). Furthermore, the display control unit 40 controls to output and display the magnified surgical field image L(x, y) monitored by the surgeon 5061 to a display device 50b (the first display region 52a) different from the display device 50a. With such a display mode, the endoscope operator 5062 and the surgeon 5061 can dispose the display devices 50a and 50b respectively at positions that are easy to view. Consequently, the surgeon 5061 can facilitate the progress of the surgery while observing the magnified surgical field image L(x, y). In addition, the endoscope operator 5062 can easily adjust the position of the endoscope 5001 while observing the surgical field image K(x, y).

As illustrated in FIG. 7, the above-described region-of-interest frame 110 and a zoom frame 112 indicating the range of the magnified surgical field image L(x, y) may be displayed within the surgical field image K(x, y). The region-of-interest frame 110 and the zoom frame 112 move within the surgical field image K(x, y) together with the movement of the endoscope 5001. In this manner, with the state in which the region-of-interest frame 110 and the zoom frame 112 are displayed within the surgical field image K(x, y), the endoscope operator 5062 can intensively confirm the surgical field image K(x, y) alone and can immediately confirm whether an appropriate range is being displayed in the magnified surgical field image L(x, y). Note that, in a case where there is no need to display the region-of-interest frame 110 and the zoom frame 112, displays of these may be independently turned ON/OFF by an operation instruction from the endoscope operator 5062.

Incidentally, the medical observation system 10a generates the three-dimensional map D(X, Y, Z) and estimates the position and orientation of the endoscope 5001, and thus, can calculate the three-dimensional position of the feature points in the vicinity of the region-of-interest. Accordingly, by applying perspective-transform and/or rotational transform on the captured surgical field image K(x, y), it is also possible to generate and display a magnified surgical field image L(x, y) in which the region-of-interest is constantly viewed in a same direction.

[Process Flow Performed by Medical Observation System According to First Embodiment]

Next, the flow of processes performed by the medical observation system 10a of the first embodiment will be described. FIG. 7 is a flowchart illustrating an example of the process flow performed by the medical observation system 10a.

Figure 8:
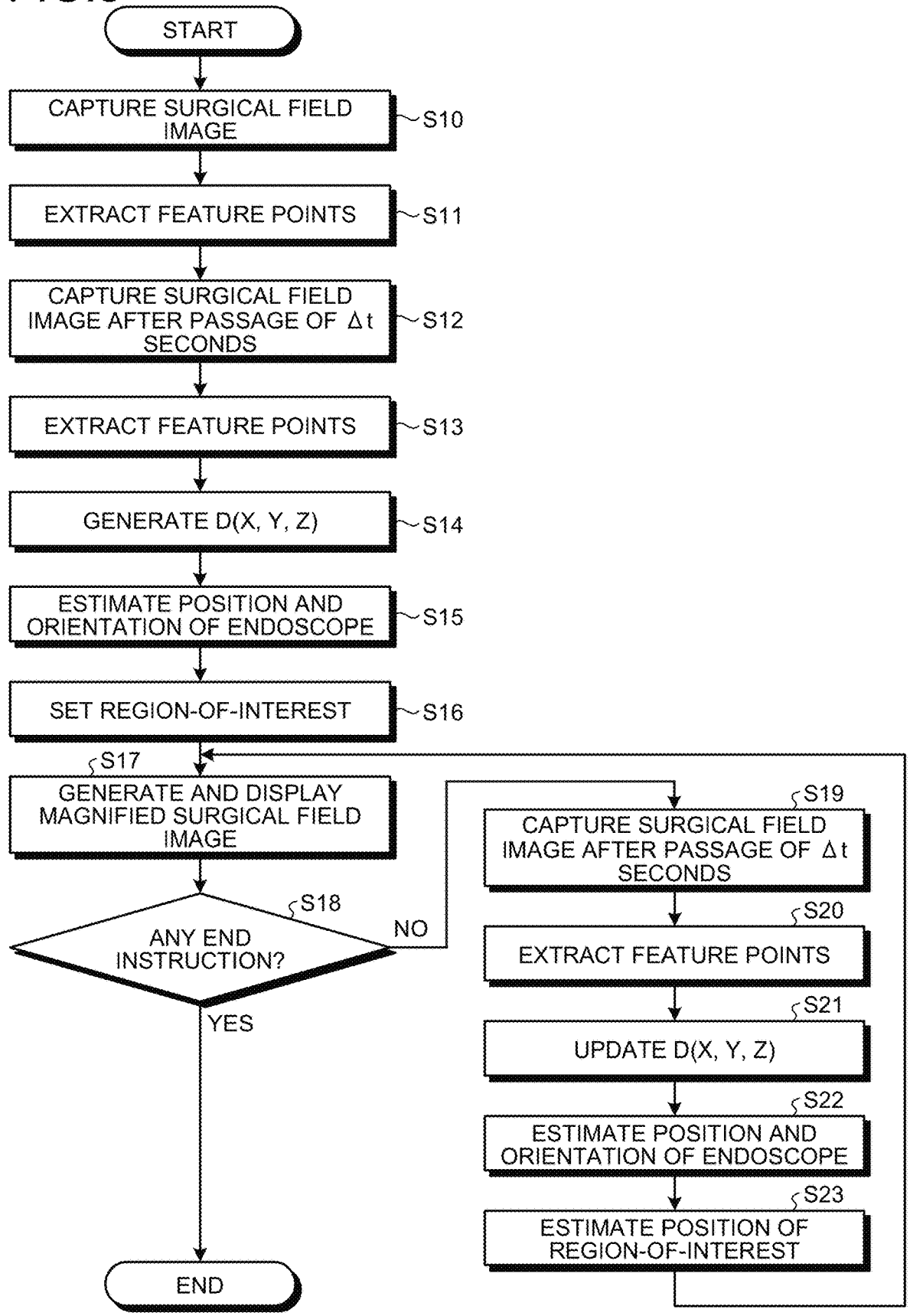
FIG. 8 is a flowchart illustrating an example of a process flow performed by a medical observation system.

Hereinafter, the flowchart of FIG. 8 will be described. First, the imaging element 44a captures a surgical field image K(x, y) (step S10).

The map generation unit 15 extracts feature points from the captured surgical field image K(x, y) (step S11).

Furthermore, the imaging element 44a captures the surgical field image K(x, y) at a predetermined timing, for example, after the passage of Δt seconds (step S12).

The map generation unit 15 extracts feature points from the captured surgical field image K(x, y) after the passage of Δt seconds (step S13).

The map generation unit 15 calculates the three-dimensional positions of the feature points and generates a three-dimensional map D(X, Y, Z) (step S14).

The self-position estimation unit 16 estimates the position and orientation of the endoscope 5001 (step S15).

The region-of-interest setting unit 20 sets the region-of-interest in the surgical field image K(x, y) (step S16).

The zoom processing unit 26 generates a magnified surgical field image L(x, y). Subsequently, the display control unit 40 controls to display the generated magnified surgical field image L(x, y) on the display device 50 (step S17).

The display control unit 40 determines whether there is an instruction to end the process (step S18). When it is determined that there is an end instruction (step S18: Yes), the medical observation system 10a ends the process of FIG. 8. In contrast, when it is not determined that there is an end instruction (step S18: No), the process proceeds to step S19. The processing end instruction is determined by detecting an operation such as turning off the power switch (not illustrated) of the camera control unit 12a, for example.

When determination of step S18 is No, the imaging element 44a captures a surgical field image K(x, y) at a predetermined timing, for example, after the passage of Δt seconds (step S19).

The map generation unit 15 extracts feature points from the captured surgical field image K(x, y) after the passage of Δt seconds (step S20).

The map generation unit 15 calculates the three-dimensional position of the feature point and updates the three-dimensional map D(X, Y, Z) generated in step S14 (step S21).

The self-position estimation unit 16 estimates the position and orientation of the endoscope 5001 (step S22).

The region-of-interest estimation unit 22 estimates the position of the region-of-interest in the surgical field image K(x, y) after the passage of Δt seconds captured in step S19 (step S23). Thereafter, the process returns to step S17.

[Operational Effects of First Embodiment]

As described above, according to the medical observation system 10a of the first embodiment, the three-dimensional information generation unit 14 generates the three-dimensional map D(X, Y, Z) (three-dimensional information) regarding the surgical field, based on the surgical field image K(x, y) captured by the imaging device 42a. The region-of-interest setting unit 20 (setting unit) then sets at least one region-of-interest in the surgical field image K(x, y) captured at a predetermined timing. Based on the three-dimensional map D(X, Y, Z) and the position of the region-of-interest set by the region-of-interest setting unit 20, the region-of-interest estimation unit 22 (estimation unit) estimates the existence position of the region-of-interest in the surgical field image K(x, y) captured at a timing different from the predetermined timing. Subsequently, the zoom processing unit 26 (magnified image generation unit) generates the magnified surgical field image L(x, y) in which the estimated region-of-interest is magnified by a predetermined magnification, and the display control unit 40 outputs at least the magnified surgical field image L(x, y). Accordingly, even when the endoscope 5001 on which the imaging device 42a is mounted has changed its position or orientation, it is possible to continuously observe the affected part in a magnified state from a distant position.

Furthermore, according to the medical observation system 10a of the first embodiment, the display control unit 40 controls to display the surgical field image K(x, y) and the magnified surgical field image L(x, y). This enables display of both the magnified surgical field image L(x, y) that the surgeon 5061 desires to view and the surgical field image K(x, y) that the endoscope operator 5062 desires to view.

Furthermore, according to the medical observation system 10a of the first embodiment, the display control unit 40 controls to display the magnified surgical field image L(x, y) and the surgical field image K(x, y) on the two display devices 50a and 50b, respectively. Therefore, the surgeon 5061 and the endoscope operator 5062 can dispose the display devices 50a and 50b respectively at positions that are easy to view.

Furthermore, according to the medical observation system 10a of the first embodiment, the region-of-interest setting unit 20 (setting unit) designates a specific position of the surgical field image K(x, y) displayed on the display device 50 by the display control unit 40, as a region-of-interest, in a state where the specific position is aligned with a predetermined position of the display device 50 and on condition that the setting signal instructing the setting of the region-of-interest has occurred. Accordingly, the region-of-interest can be easily and reliably set by regular operations.

Furthermore, according to the medical observation system 10a of the first embodiment, the region-of-interest setting unit 20 (setting unit) sets a region-of-interest on the position instructed by the input device, on the surgical field image K(x, y) displayed on the display device 50 by the display control unit 40. Therefore, the region-of-interest can be easily and reliably set by an intuitive operation.

Furthermore, according to the medical observation system 10a of the first embodiment, the imaging device 42a includes one imaging element 44a, and the three-dimensional information generation unit 14 generates the three-dimensional map D(X, Y, Z) (three-dimensional information) of the surgical field based on at least two surgical field images K(x, y) captured by the imaging device 42a at different times. This makes it possible to continuously observe the affected part in a magnified state from a distant position by using the imaging device 42a having a simple configuration with a monocular camera alone.

Furthermore, according to the medical observation system 10a of the first embodiment, the imaging device 42a is mounted on the endoscope 5001. Therefore, when performing an operation or the like using the endoscope 5001, the surgeon 5061 can stably observe the affected part in a magnified state.

Furthermore, according to the camera control unit 12a (medical observation apparatus) of the first embodiment, the three-dimensional information generation unit 14 generates the three-dimensional map D(X, Y, Z) (three-dimensional information) of the surgical field based on the surgical field image K(x, y) obtained by capturing the surgical field. Subsequently, the region-of-interest setting unit 20 (setting unit) sets at least one region-of-interest within the surgical field image K(x, y) captured at a certain time. Based on the three-dimensional map D(X, Y, Z) and the position of the region-of-interest set by the region-of-interest setting unit 20, the region-of-interest estimation unit 22 (estimation unit) estimates the existence position of the region-of-interest from within the surgical field image K(x, y) captured at a time different from the above-described time. Subsequently, the zoom processing unit 26 (magnified image generation unit) generates the magnified surgical field image L(x, y) in which the estimated region-of-interest is magnified by a predetermined magnification, and the display control unit 40 controls to display at least the magnified surgical field image L(x, y). This makes it possible to continuously observe the affected part in a magnified state.

In the medical observation system 10a, the endoscope 5001 incorporating the imaging device 42a may be equipped with an acceleration sensor such as a gyro sensor. By monitoring the output of the acceleration sensor, the position and orientation of the endoscope 5001 can be measured in real time. This would make it possible to measure the position and orientation of the endoscope 5001 without capturing two images at different times by the imaging device 42a, enabling estimation of the position of the region-of-interest.

Second Embodiment

The configuration of the medical observation system 10a is not limited to the configuration described in the first embodiment, and various modifications can be implemented. Hereinafter, other embodiments of the medical observation system will be described one by one.

FIG. 9 is a view illustrating an example of a display mode of an image output by the display control unit 40 to the display device 50. That is, the first embodiment includes exemplary cases where the display control unit 40 outputs the magnified surgical field image L(x, y) alone to the display device 50, and where the magnified surgical field image L(x, y) and the surgical field image K(x, y) are output to the mutually different display devices 50a and 50b, respectively. However, the display modes of output images are not limited to these.

FIG. 9A illustrates an example in which the display control unit 40 controls to display the surgical field image K(x, y) and the magnified surgical field image L(x, y) adjacent to each other (side by side) on the display device 50. That is, the magnified surgical field image L(x, y) is displayed in the first display region 52a and the surgical field image K(x, y) is displayed in the second display region 52b, which are set on the display screen of the display device 50. With such a display mode, the surgeon 5061 can proceed with the operation while observing the magnified surgical field image L(x, y), and the endoscope operator 5062 can adjust the position of the endoscope 5001 while observing the surgical field image K(x, y).

FIG. 9B is an example in which the display control unit 40 controls to display, on the display device 50, an image obtained by superimposing (using PinP) the surgical field image K(x, y) on a part of the magnified surgical field image L(x, y). In this case, the second display region 52b is superimposed on a part of the first display region 52a. With such a display mode, the surgeon 5061 can proceed with the operation while observing the magnified surgical field image L(x, y), and the endoscope operator 5062 can adjust the position of the endoscope 5001 while observing the surgical field image K(x, y). The position where the surgical field image K(x, y) is superimposed is not limited to the example of FIG. 9B, and may be any of the upper left, upper right, and lower right positions of the magnified surgical field image L(x, y).

[Operational Effects of Second Embodiment]

In this manner, according to the second embodiment, the display control unit 40 controls to display the surgical field image K(x, y) and the magnified surgical field image L(x, y) on one display device 50, with the two images adjacent to each other. This enables display of both the magnified surgical field image L(x, y) that the surgeon 5061 desires to view and the surgical field image K(x, y) that the endoscope operator 5062 desires to view.

In this manner, according to the second embodiment, the display control unit 40 controls to display the surgical field image K(x, y) so as to be superimposed on a part of the magnified surgical field image L(x, y), on one display device 50. This enables display of both the magnified surgical field image L(x, y) that the surgeon 5061 desires to view and the surgical field image K(x, y) that the endoscope operator 5062 desires to view. In particular, the magnified surgical field image L(x, y) can be displayed as large as possible.

Third Embodiment

Figure 10:
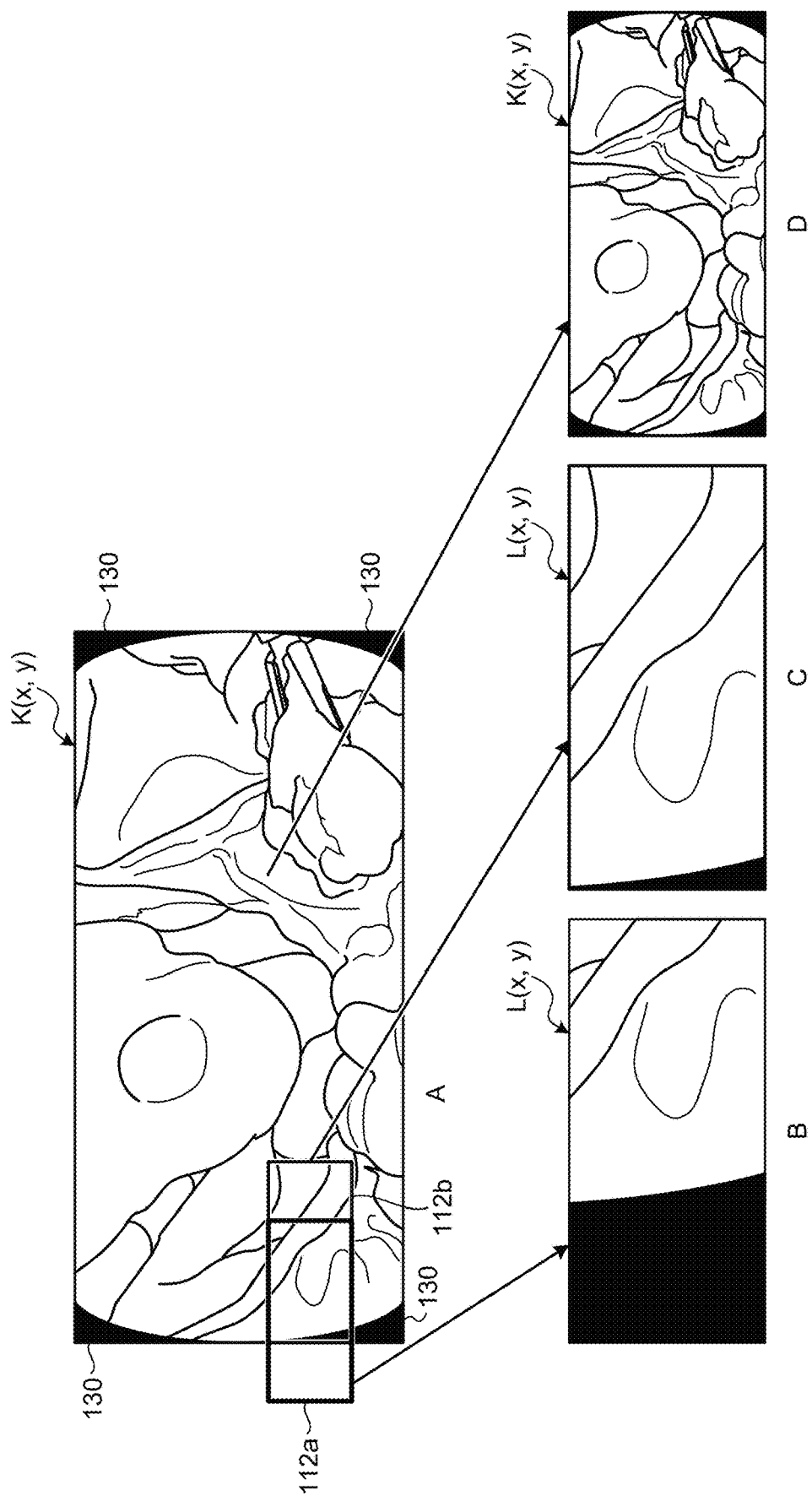
FIG. 10 is a view illustrating an example of a process performed when a zoom frame reaches an edge of a surgical field image with the movement of an endoscope.

FIG. 10 is a view illustrating an example of a process performed when a zoom frame reaches an edge of the surgical field image K(x, y) with the movement of the endoscope 5001. The zoom frame is a frame indicating a display range of the magnified surgical field image L(x, y).

Here, since the endoscope 5001 has a tubular shape having a circular cross section, the surgical field image K(x, y) observed by the endoscope 5001 includes vignetting regions 130 having circular shadings, in peripheral portions in the image. Since the vignetting regions 130 are regions formed by the absence of light, they are observed as black regions as illustrated in FIG. 10A.

In a case where the endoscope operator 5062 moves the endoscope 5001, the zoom frame might reach the edge of the surgical field image K(x, y). In this case, the medical observation system 10a takes one of three processing modes prepared in advance.

FIG. 10B is an example in which when a zoom frame 112a reaches the edge of the surgical field image K(x, y), the region without image information is displayed in black. That is, the zoom processing unit 26 generates a magnified surgical field image L(x, y) in which a predetermined pixel value (for example, pixel value zero representing black) is stored in the region of the zoom frame 112a exceeding the edge of the surgical field image K(x, y) and overlapping with the vignetting region 130. Subsequently, the display control unit 40 controls to display the generated magnified surgical field image L(x, y).

Specifically, when the zoom frame 112a has reached the position illustrated in FIG. 10A, the display control unit 40 controls to display the magnified surgical field image L(x, y) in which a pixel value of zero indicating the color of black is interpolated to the region inside the zoom frame 112a where the image information is missing. With such a display mode, the endoscope operator 5062 can immediately recognize that the position of the endoscope 5001 has reached the edge of the surgical field image K(x, y) because of expansion of the black region. The endoscope operator 5062 can regenerate the magnified surgical field image L(x, y) without any vignetting by adjusting the position of the endoscope 5001.

FIG. 10C is an example in which the screen edge is continuously displayed as it is when the zoom frame 112a has reached the edge of the surgical field image K(x, y). That is, in a case where the edge of the zoom frame 112a, that is, the edge of the magnified surgical field image L(x, y) is aligned with the edge of the surgical field image K(x, y), the zoom processing unit 26 generates the magnified surgical field image L(x, y) while holding the position of the zoom frame 112a even in a case where the endoscope 5001 has further moved beyond the edge of the surgical field image K(x, y). Subsequently, the display control unit 40 controls to display the generated magnified surgical field image L(x, y).

Specifically, in a case where the zoom frame 112a has reached the position illustrated in FIG. 10A, the display control unit 40 controls to move the zoom frame 112a to the position of a zoom frame 112b so as to display the image inside the moved zoom frame 112b as a magnified surgical field image L(x, y). That is, at this time, the left end of the zoom frame 112b is aligned with the left end of the surgical field image K(x, y). By adopting such a display mode, the display region of the magnified surgical field image L(x, y) can be held at the end of the surgical field image K(x, y) regardless of the movement of the endoscope 5001.

FIG. 10D illustrates an example in which the zoom processing unit 26 stops the generation of the magnified surgical field image L(x, y) in a case where the zoom frame 112a has reached the end of the surgical field image K(x, y). At this time, the display control unit 40 controls to display the surgical field image K(x, y).

By adopting such a display mode, the display of the magnified surgical field image L(x, y) is canceled, and whereby the endoscope operator 5062 can immediately recognize the fact that the imaging range of the endoscope 5001 has reached the end of the surgical field image K(x, y). The endoscope operator 5062 can regenerate the magnified surgical field image L(x, y) without any vignetting by adjusting the position of the endoscope 5001.

Note that which of the above-described processes is to be performed when the zoom frame 112a has reached the end of the surgical field image K(x, y) is preferably set in advance in the zoom processing unit 26.

[Operational Effects of Third Embodiment]

In this manner, according to the third embodiment, in a case where the zoom frame 112a has reached the edge of the surgical field image K(x, y), or comes to a position to overlap the vignetting region of the surgical field image K(x, y), the zoom processing unit 26 (magnified image generation unit) generates the magnified surgical field image L(x, y) that stores a predetermined pixel value in the region beyond the edge and the region overlapping the vignetting region in the zoom frame 112a. Therefore, the endoscope operator 5062 can immediately recognize the fact that the zoom frame 112a has reached the edge of the surgical field image K(x, y). The endoscope operator 5062 can also adjust the position of the endoscope 5001 to suppress an occurrence of vignetting.

Furthermore, according to the third embodiment, in a case where the zoom frame 112a has reached the edge of the surgical field image K(x, y), the zoom processing unit 26 (magnified image generation unit) generates a magnified surgical field image L(x, y) in which the edge of the magnified surgical field image L(x, y) is aligned with the edge of the surgical field image K (x, y). Therefore, it is possible to continuously display the magnified surgical field image L (x, y) without any vignetting.

Furthermore, according to the third embodiment, the zoom processing unit 26 (magnified image generation unit) stops generation of the magnified surgical field image L(x, y) in a case where the zoom frame 112a has reached the edge of the surgical field image K(x, y) or comes to a position overlapping the vignetting region of the surgical field image K(x, y). Therefore, the endoscope operator 5062 can immediately recognize the fact that the imaging range of the endoscope 5001 has reached the edge of the surgical field image K(x, y). The endoscope operator 5062 can also adjust the position of the endoscope 5001 to suppress an occurrence of vignetting.

Fourth Embodiment

In the first embodiment, the medical observation system 10a has been described assuming that the imaging device 42a has one imaging element 44a. However, the configuration of the imaging device is not limited to this.

Figure 11:
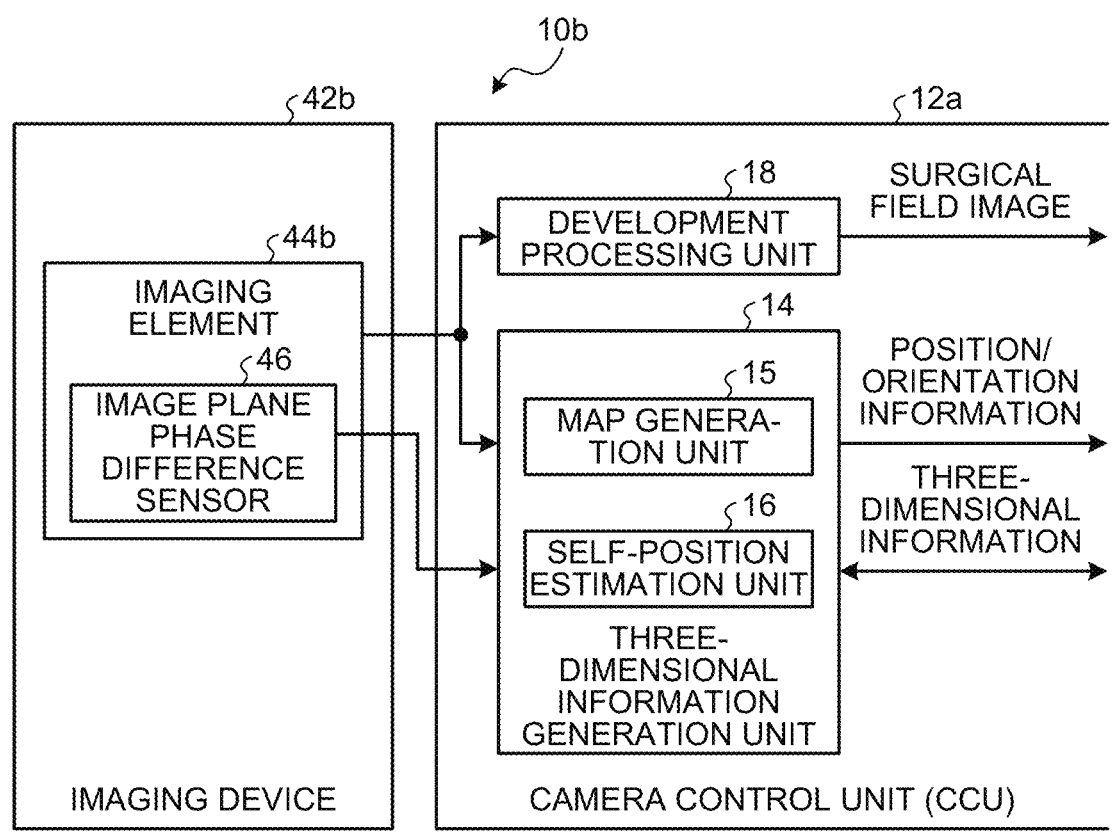
FIG. 11 is a diagram illustrating an example of a schematic configuration of a medical observation system in which an imaging device includes an imaging element having an image plane phase difference sensor.

FIG. 11 is a diagram illustrating an example of a schematic configuration of a medical observation system 10b in which an imaging device 42b includes an imaging element 44b having an image plane phase difference sensor 46. Note that a part of illustration corresponding to FIG. 2 is omitted in FIG. 11. Accordingly, unless otherwise specified, the omitted portion has the same configuration as that of FIG. 2.

The image plane phase difference sensor 46 has a configuration in which pixels for distance measurement are discretely arranged in the imaging element 44b. By using the medical observation system 10b configured as illustrated in FIG. 11, the map generation unit 15 can extract depth information (distance information), that is, information regarding a depth (distance) to an imaged object 100 from the image plane phase difference information output by the image plane phase difference sensor 46. This leads to effective utilization of SLAM technology. Note that the image plane phase difference sensor 46 can obtain depth information from a single captured image.

In this manner, according to the fourth embodiment, the depth information can be obtained from one captured surgical field image K(x, y). This makes it possible to measure the three-dimensional position of an object with high accuracy even when the object is moving.

Fifth Embodiment

Figure 12:
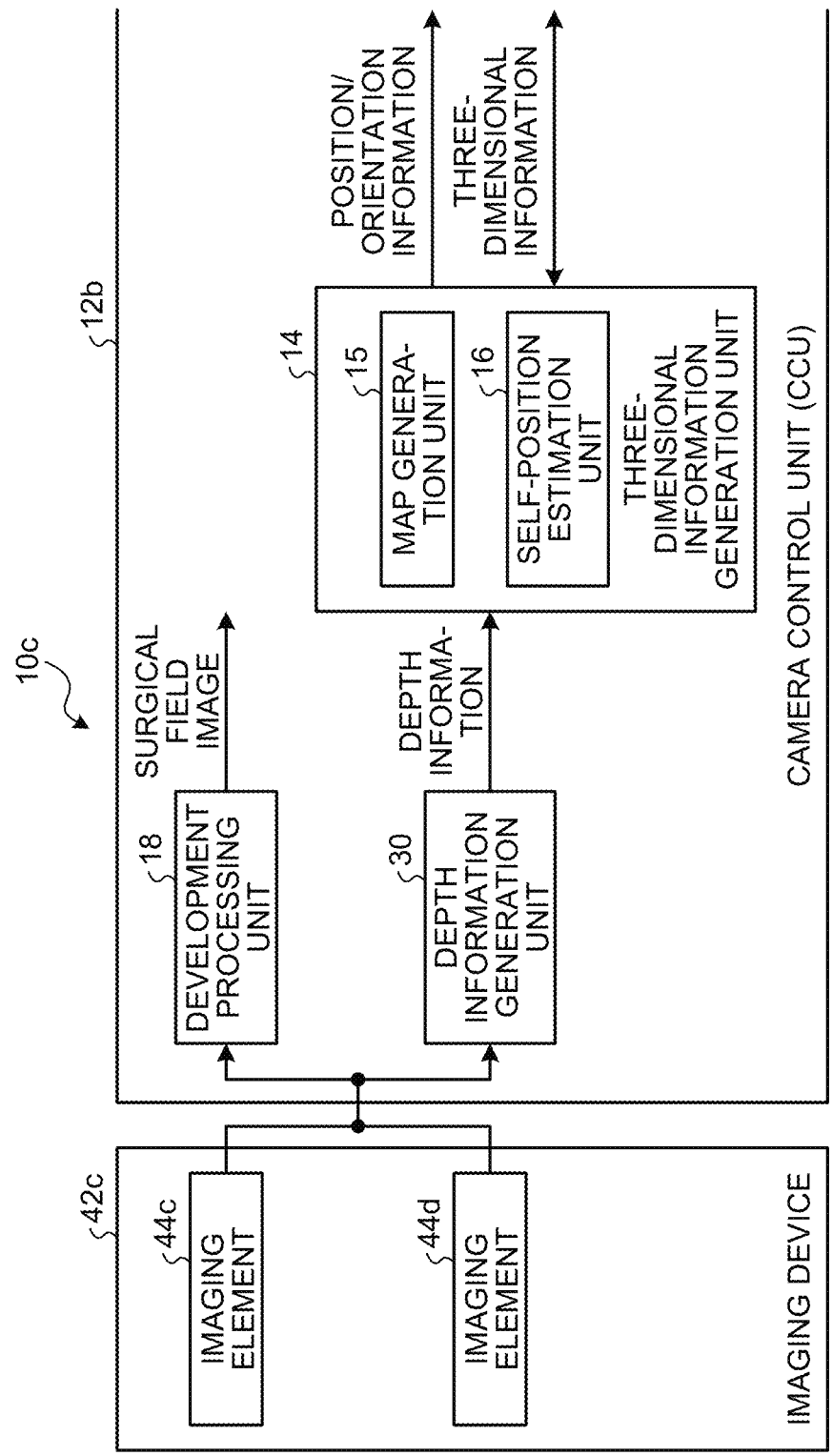
FIG. 12 is a diagram illustrating an example of a schematic configuration of a medical observation system in which an imaging device includes two imaging elements.

FIG. 12 is a diagram illustrating an example of a schematic configuration of a medical observation system 10c in which an imaging device 42c includes two imaging elements 44c and 44d. The two imaging elements 44c and 44d are arranged in a state of maintaining a predetermined relative relationship and capture images of different locations of an affected part so as to partially overlap each other. More specifically, the imaging elements 44c and 44d respectively acquire image signals for the right eye and the left eye, corresponding to stereoscopic vision. Note that a part of illustration corresponding to FIG. 2 is omitted in FIG. 12. Accordingly, unless otherwise specified, the omitted portion has the same configuration as that of FIG. 2.

Furthermore, in the medical observation system 10c, the camera control unit 12b includes a depth information generation unit 30 in addition to the configuration described with reference to FIG. 2. The depth information generation unit 30 generates depth information by matching two surgical field images individually captured by the two imaging elements 44c and 44d.

By using the medical observation system 10c configured as illustrated in FIG. 12, the map generation unit 15 can generate the three-dimensional map D(X, Y, Z) by using the depth information generated by the depth information generation unit 30 and the surgical field images individually captured by the imaging elements 44c and 44d, with application of the SLAM technology. Furthermore, since the two imaging elements 44c and 44d can perform imaging at the same time, depth information can be obtained from the two images obtained by one shot of imaging. Therefore, even when the object is moving, the three-dimensional position of the object can be measured with high accuracy.

In this manner, according to the fifth embodiment, the imaging device 42c includes the two imaging elements 44c and 44d that image different ranges partially overlapping each other, and the three-dimensional information generation unit 14 generates three-dimensional information of the surgical field based on the two surgical field images K(x, y) captured by the two imaging elements 44c and 44d at the same time. Therefore, depth information can be obtained from the two surgical field images K(x, y) obtained by one imaging, making it possible to measure the three-dimensional position of the surgical field with high accuracy even when the surgical field is moving.

Sixth Embodiment

Figure 13:
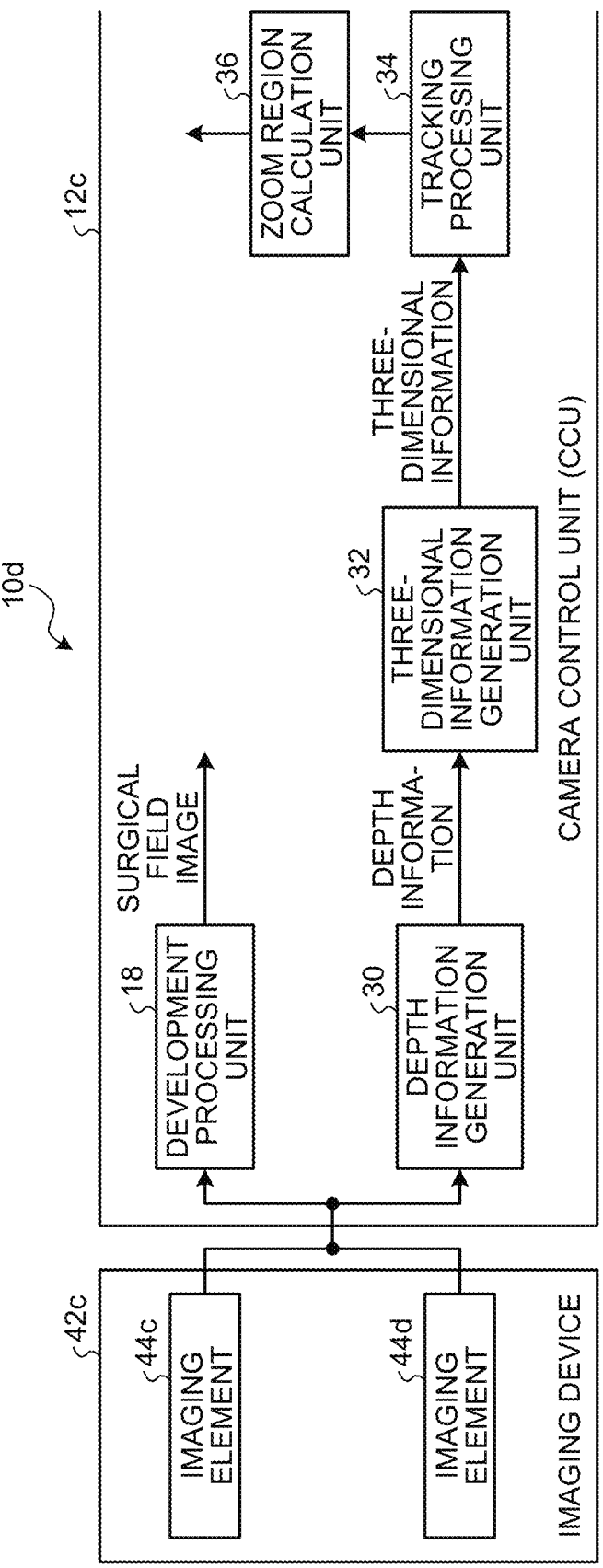
FIG. 13 is a diagram illustrating an example of a schematic configuration of a medical observation system in which an imaging device includes two imaging elements, and a camera control unit includes a tracking processing unit.

FIG. 13 is a diagram illustrating an example of a schematic configuration of a medical observation system 10d in which the imaging device 42c includes two imaging elements, and a camera control unit 12c includes a tracking processing unit 34. Note that a part of illustration corresponding to FIG. 2 is omitted in FIG. 13. Accordingly, unless otherwise specified, the omitted portion has the same configuration as that of FIG. 2.

The camera control unit 12c of the medical observation system 10d includes a depth information generation unit 30, a three-dimensional information generation unit 32, a tracking processing unit 34, and a zoom region calculation unit 36.

The three-dimensional information generation unit 32 is provided in place of the three-dimensional information generation unit 14 (FIG. 2), and generates three-dimensional information of the surgical field image K(x, y) based on the depth information generated by the depth information generation unit 30. The tracking processing unit 34 is provided in place of the three-dimensional map data storage unit 24 (FIG. 2), and calculates a difference in position and orientation of the imaging device 42c using a method of superimposing two point clouds, such as iterative closest point (ICP) method, based on three-dimensional information of the immediately preceding frame and three-dimensional information of the current frame. The zoom region calculation unit 36 is provided in place of the region-of-interest estimation unit 22 (FIG. 2), and calculates coordinates of the region-of-interest on the screen based on a difference value of the position/orientation of the imaging device 42c calculated by the tracking processing unit 34. Subsequently, the zoom processing unit 26 (FIG. 2) described above performs zoom processing on the region calculated by the zoom region calculation unit 36, and generates a magnified surgical field image L(x, y).

In this manner, according to the sixth embodiment, the region-of-interest in the surgical field image K(x, y) can be stably tracked (followed) regardless of the movement of the imaging device 42c.

Seventh Embodiment

Figure 14:
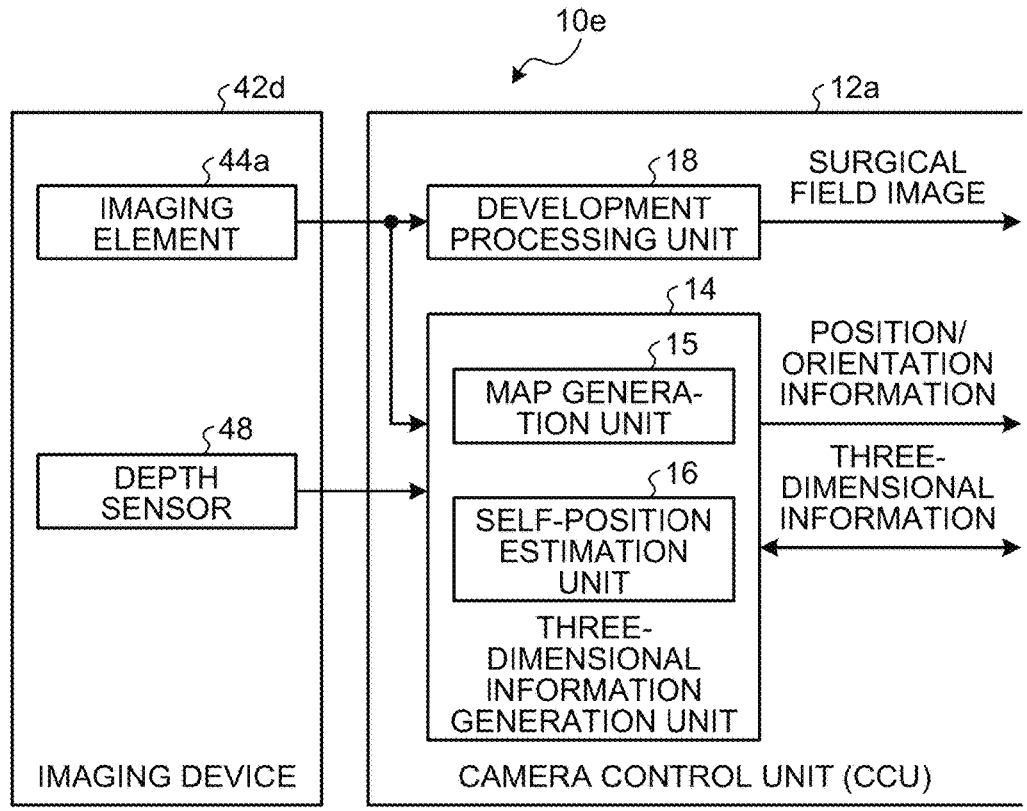
FIG. 14 is a diagram illustrating an example of a schematic configuration of a medical observation system in which an imaging device includes an imaging element and a depth sensor.

FIG. 14 is a diagram illustrating an example of a schematic configuration of a medical observation system 10e in which an imaging device 42d includes an imaging element 44a and a depth sensor 48. Note that a part of illustration corresponding to FIG. 2 is omitted in FIG. 14. Accordingly, unless otherwise specified, the omitted portion has the same configuration as that of FIG. 2.

The depth sensor 48 is also referred to as a 3D sensor that measures the distance to the subject. The depth sensor 48 is also referred to as a time of flight (ToF) sensor that receives reflected light of infrared light, for example, emitted toward the subject, and thereby measures the flight time of light to obtain the distance to the subject. Furthermore, the depth sensor 48 is actualized by using a pattern projection method (Structured Light projection) in which an image of projected light having a plurality of different geometric patterns applied to the subject is captured so as to measure the distance to the subject.

The map generation unit 15 extracts depth information (distance information) to the captured object 100 based on the surgical field image K(x, y) captured by the imaging element 44a and the distance output by the depth sensor 48. More specifically, the map generation unit 15 calculates which pixel of the surgical field image K(x, y) captured by the imaging element 44a corresponds to the point measured by the depth sensor 48. Subsequently, the map generation unit 15 generates a three-dimensional map D(X, Y, Z) (three-dimensional information) of the surgical field. This leads to effective utilization of SLAM technology.

In this manner, according to the seventh embodiment, the imaging device 42d includes the one imaging element 44a and the depth sensor 48 (distance measuring device) that measures the distance to the object, and the three-dimensional information generation unit 14 generates the three-dimensional map D(X, Y, Z) (three-dimensional information) of the surgical field based on the image captured by the imaging element 44a and the distance measured by the depth sensor 48. This makes it possible to measure the distance to the surgical field easily and reliably.

Eighth Embodiment

Figure 15:
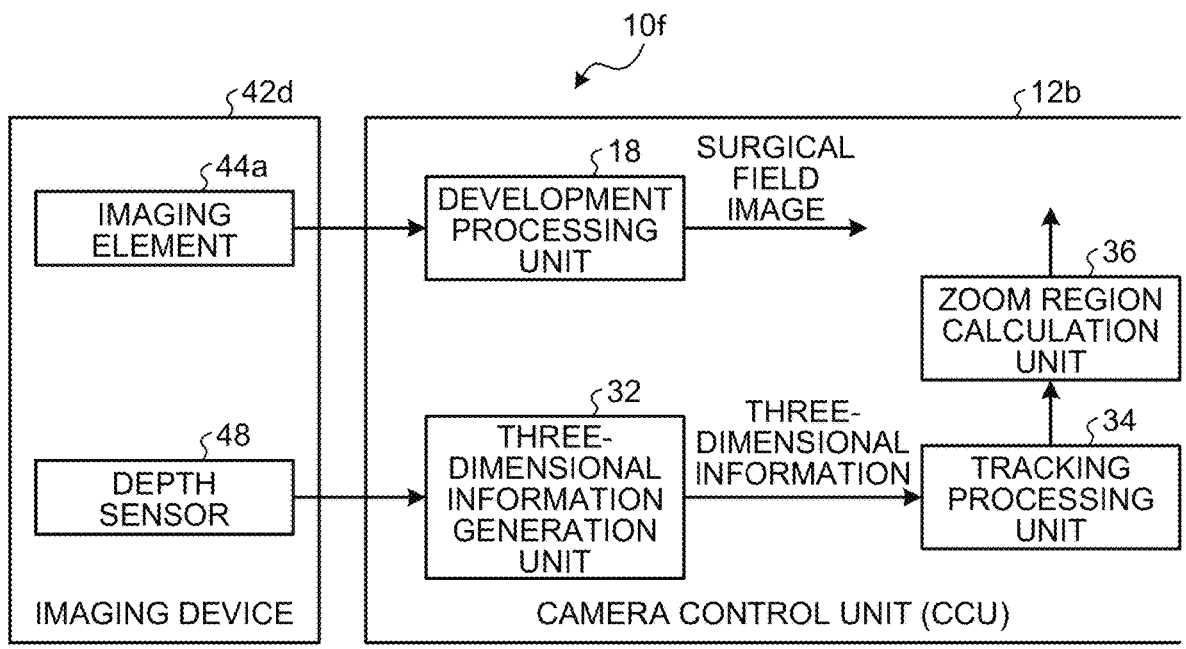
FIG. 15 is a diagram illustrating an example of a schematic configuration of a medical observation system in which an imaging device includes an imaging element and a depth sensor, and a camera control unit includes a tracking processing unit.

FIG. 15 is a diagram illustrating an example of a schematic configuration of a medical observation system 10f in which an imaging device 42d includes an imaging element 44a and a depth sensor 48, and a camera control unit 12d includes a tracking processing unit 34. Note that a part of illustration corresponding to FIG. 2 is omitted in FIG. 15. Accordingly, unless otherwise specified, the omitted portion has the same configuration as that of FIG. 2.

The camera control unit 12d of the medical observation system 10f includes a three-dimensional information generation unit 32, a tracking processing unit 34, and a zoom region calculation unit 36.

The three-dimensional information generation unit 32 is provided in place of the three-dimensional information generation unit 14 (FIG. 2), and performs matching of two pieces of distance information (for example, distance images storing pixel values corresponding to the distance to the subject) measured by the depth sensor 48 from different positions, thereby obtaining the moving state of the surgical field. The tracking processing unit 34 is provided in place of the three-dimensional map data storage unit 24 (FIG. 2), and calculates a difference in position/orientation of the imaging device 42c based on the moving state of the surgical field described above. The zoom region calculation unit 36 is provided in place of the region-of-interest estimation unit 22 (FIG. 2), and calculates coordinates of the region-of-interest on the screen based on a difference value of the position/orientation of the imaging device 42c calculated by the tracking processing unit 34. Subsequently, the zoom processing unit 26 (FIG. 2) described above performs zoom processing on the region calculated by the zoom region calculation unit 36, and generates a magnified surgical field image L(x, y).

In this manner, according to the eighth embodiment, the region-of-interest in the surgical field image K(x, y) can be stably tracked (followed) regardless of the movement of the imaging device 42d.

Ninth Embodiment

Figure 16:
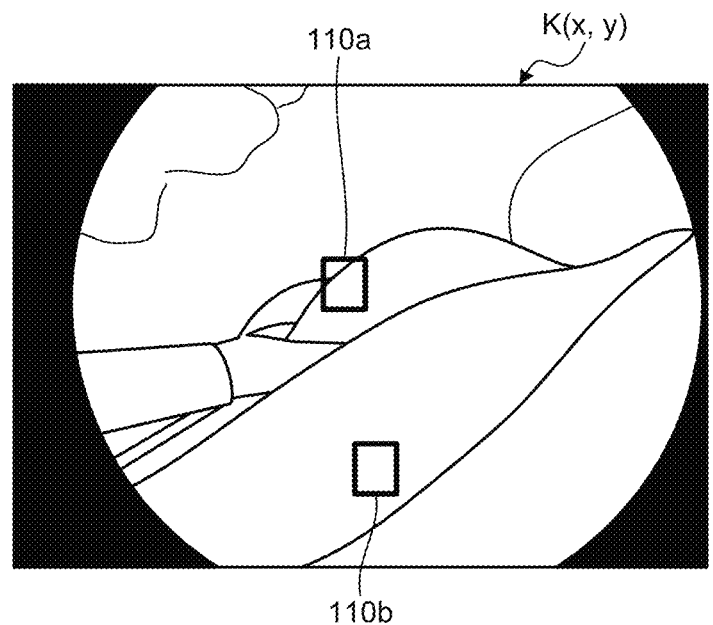
FIG. 16 is a view illustrating an example in which a plurality of regions-of-interest is set in a surgical field image.

FIG. 16 is a view illustrating an example in which a plurality of region-of-interest frames 110a and 110b is set in the surgical field image K(x, y).

As illustrated in FIG. 16, the region-of-interest setting unit 20 (FIG. 2) may set a plurality of regions-of-interest in the surgical field image K(x, y). For example, when it is necessary to pay attention to a plurality of affected parts, the region-of-interest setting unit 20 sets region-of-interest frames 110a and 110b indicating individual regions-of-interest based on an instruction from the endoscope operator 5062. Subsequently, the display control unit 40 controls to individually display, on the display device 50, two magnified surgical field images L(x, y) in which the region of the zoom frame corresponding to each of the region-of-interest frames 110a and 110b is magnified.

In this manner, according to the ninth embodiment, in a case of having a plurality of regions-of-interest in the surgical field, the region-of-interest setting unit 20 sets a plurality of regions-of-interest. Therefore, it is possible to display the magnified surgical field image L(x, y) in which a plurality of regions-of-interest is magnified.

Tenth Embodiment

Figure 17:
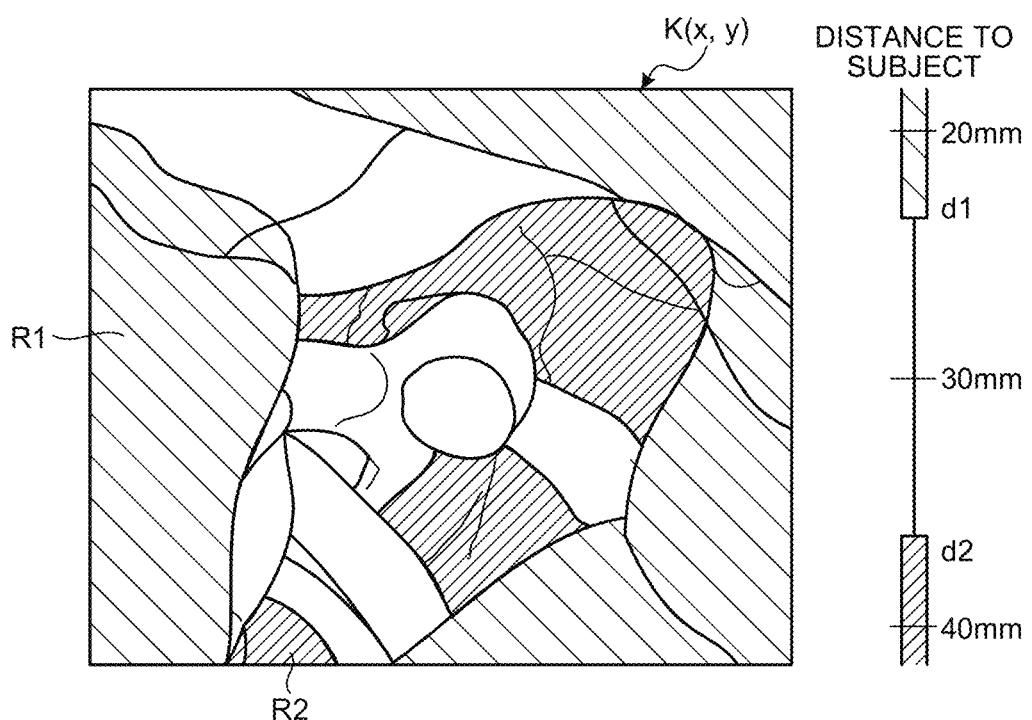
FIG. 17 is a view illustrating an example in which a region in a predetermined distance range is presented by highlighted display in a surgical field image.

FIG. 17 is a view illustrating an example in which a region in a predetermined distance range is presented by highlighted display in a surgical field image K(x, y).

When setting the region-of-interest, the region-of-interest setting unit 20 displays a predetermined distance range region in the surgical field image K(x, y) with a predetermined coloring, as illustrated in FIG. 17. FIG. 17 illustrates an example in which a region R1 having a distance shorter than a distance d1 and a region R2 having a distance longer than a distance d2 are displayed in different colors. Note that this is a process performed to restrict a distance range to the region-of-interest to a range from the distance d1 to the distance d2, for the purpose of facilitating the setting of the region-of-interest.

The values of the distance d1 and the distance d2 can be preferably set, as illustrated in FIG. 17, using a method in which the region-of-interest setting unit 20 controls to display a distance scale in the vicinity of the surgical field image K(x, y), and the endoscope operator 5062 manipulates an input device such as a mouse or a touch panel. In accordance with the set values of the distance d1 and the distance d2, the region-of-interest setting unit 20 performs real time coloring display of the region R1 and the region R2 on the surgical field image K(x, y). At this time, the manipulator points, with the input device, to the position of the distance to be set on the distance scale so as to set the distance d1 or the distance d2. The manipulator next drags the input device toward the farther direction or the closer direction on the distance scale while performing the pointing with the input device. By detecting this drag operation, the region-of-interest setting unit 20 displays a color attached in the dragged distance range on the distance scale as illustrated in FIG. 17. With this graphical user interface (GUI), the manipulator can easily recognize the region corresponding to the distance range set by oneself, in the surgical field image K(x, y). Note that the method of displaying the set distance range on the distance scale is not limited to the method illustrated in FIG. 17, and other display modes may be used as long as the set distance range is clearly indicated.

The display control unit 40 controls to display, on the display device 50, the surgical field image K(x, y) in which the region R1 and the region R2 are displayed with individual colors. The endoscope operator 5062 sets the region-of-interest following the above procedure (refer to FIG. 4) while viewing the surgical field image K(x, y) in which the region R1 and the region R2 are displayed in individual colors.

In this manner, according to the tenth embodiment, the region-of-interest setting unit 20 (setting unit) further includes a function of designating a distance range containing a region-of-interest, and sets the region-of-interest within the designated distance range. Accordingly, the endoscope operator 5062 can set the region-of-interest more easily.

Eleventh Embodiment

Figure 18:
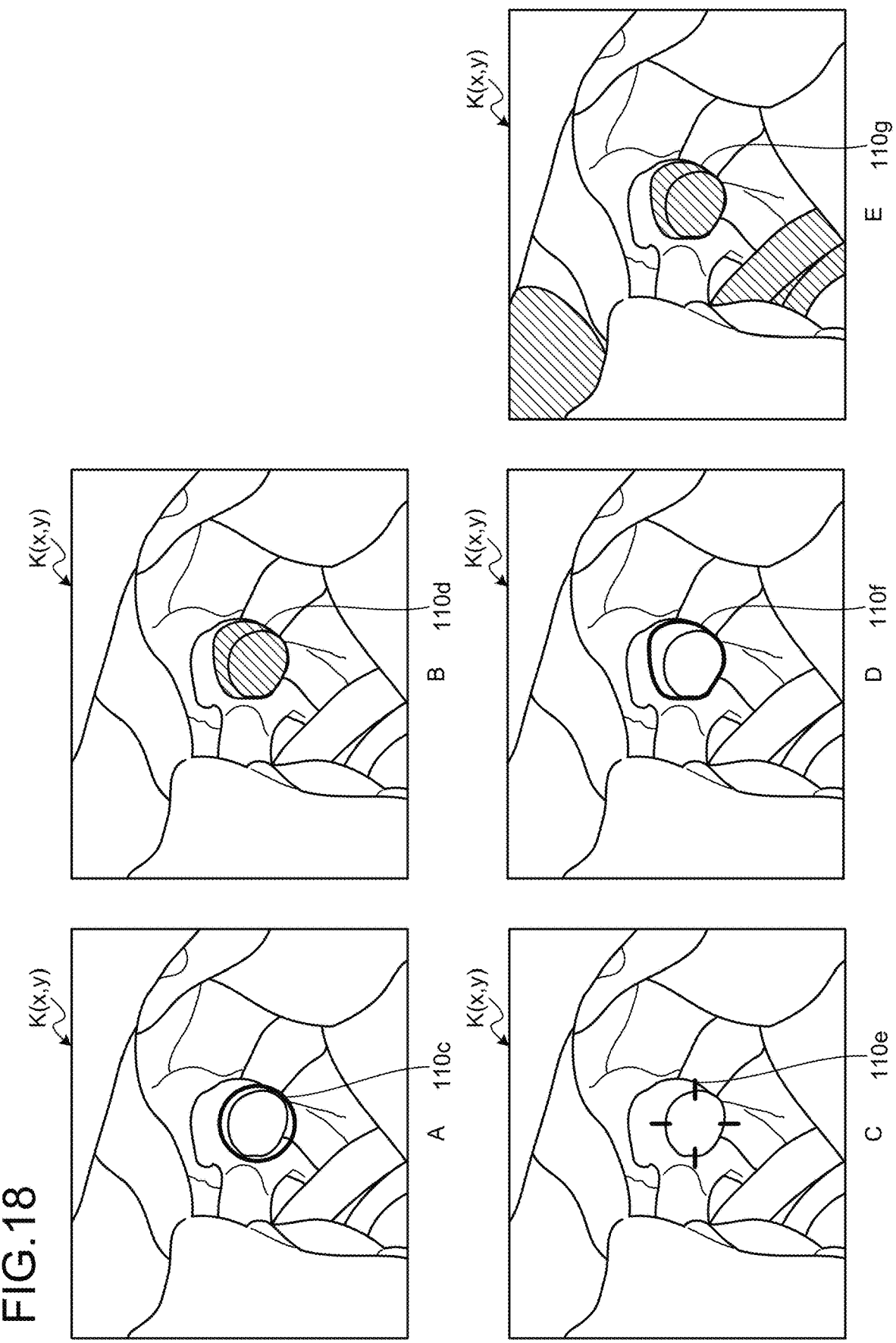
FIG. 18 is a view illustrating an example of a display mode of a region-of-interest frame set in a surgical field image.

FIG. 18 is a view illustrating an example of a display mode of region-of-interest frames 110c to 110g set in the surgical field image K(x, y).

The display mode of the region-of-interest frame is not limited to the rectangular frame illustrated in FIG. 4. FIG. 18A is an example in which the region-of-interest frame 110c is displayed in a circular region. FIG. 18B is an example in which the region-of-interest frame 110d is illustrated as a colored (highlighted) closed region. FIG. 18C is an example in which the region-of-interest frame 110e is illustrated as a symbol. FIG. 18D is an example in which the region-of-interest frame 110f is illustrated as a closed curve. FIG. 18E is an example in which the region-of-interest frame 110g and regions having the same distance as the set position of the region-of-interest frame 110g are both displayed with coloring. According to the display mode of FIG. 18E in particular, the endoscope operator 5062 can recognize that other regions exist at a same distance position as the region-of-interest. This enables gripping the endoscope 5001 further carefully so as to avoid interrupting the tracking to the region-of-interest in a case where the endoscope 5001 is erroneously oriented in a direction of another region.

Note that the endoscope operator 5062 is only required to preliminarily set, in the region-of-interest setting unit 20, in which mode the region-of-interest frame is to be displayed. The method of setting the region-of-interest frames 110c to 110g are to preferably be set following the method described with reference to FIG. 4 or 5. In a case where the region-of-interest frame is set as a closed region having an arbitrary shape, in particular, as illustrated in FIGS. 18B, 18D, and 18E, it is efficient to directly set the position and shape of the region-of-interest frame on the surgical field image K(x, y) displayed on the display device 50, as illustrated in FIG. 5.

In this manner, according to the eleventh embodiment, the region-of-interest frames 110c to 110g of a mode with high visibility for the manipulator can be displayed in the set region-of-interest.

Twelfth Embodiment

Figure 19:
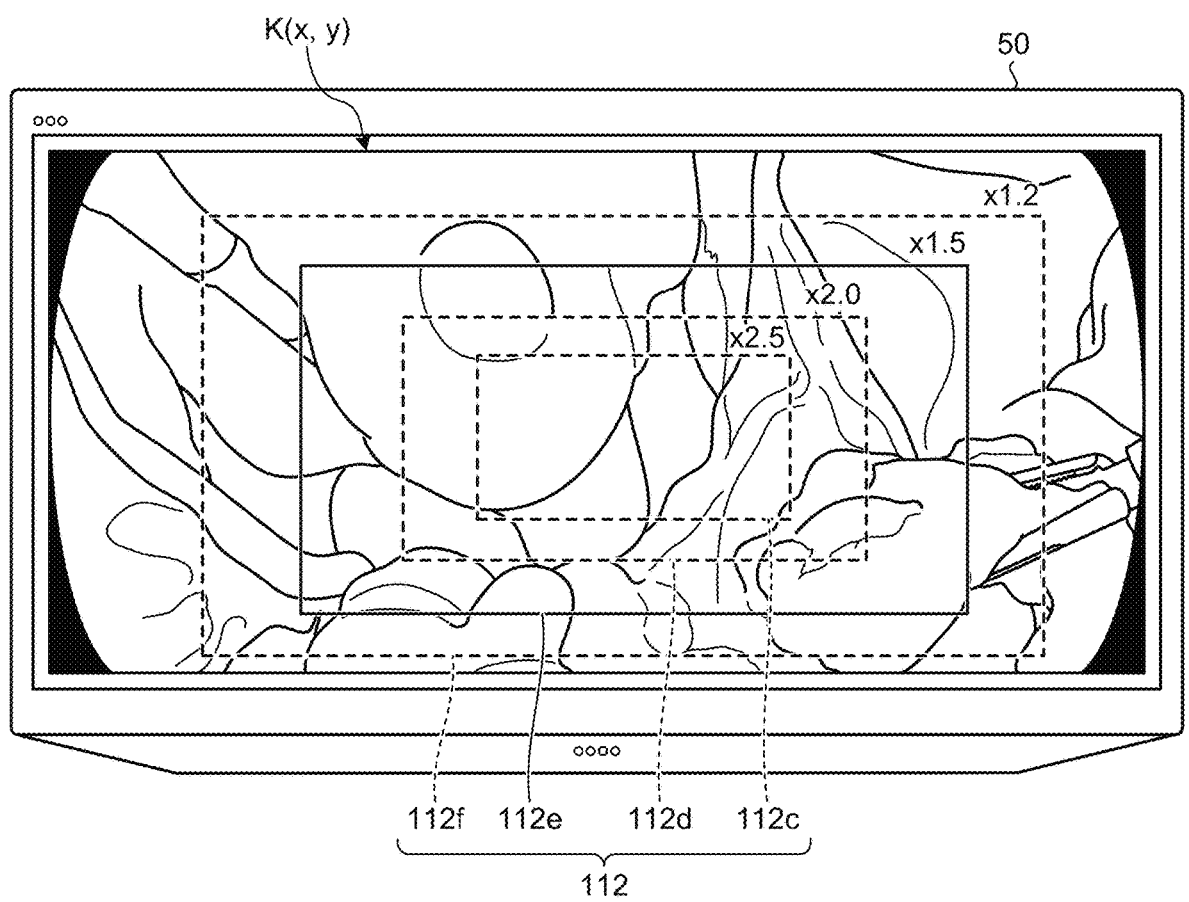
FIG. 19 is a view illustrating an example of a method for setting the zoom frame.

FIG. 19 is a diagram illustrating an example of a method for setting the zoom frame 112.

At the start of use of the medical observation system 10a, the endoscope operator 5062 may set the magnification used for magnifying the surgical field image K(x, y). Setting of magnification can be performed by a method, for example, in which the zoom processing unit 26 in FIG. 2 causes the display control unit 40 to display a plurality of selectable zoom frames 112 (112c to 112f) to be superimposed on the surgical field image K(x, y) on the display device 50 so as to allow the manipulator to designate one of the zoom frames. FIG. 19 illustrates an example in which the zoom frame 112e indicating 1.5× magnification is designated. The zoom frame 112 can be selected, for example, by operating an input device such as a hand switch provided near the endoscope 5001.

Furthermore, the zoom processing unit 26 may generate the magnified surgical field image L(x, y) at a magnification appropriate for the distance to the region-of-interest. That is, the zoom processing unit 26 calculates the distance to the region-of-interest, for example, based on the three-dimensional map D(X, Y, Z) generated by the three-dimensional information generation unit 14 and stored in the three-dimensional map data storage unit 24. Subsequently, the magnification used for generating the magnified surgical field image L(x, y) is determined in accordance with the calculated distance to the region-of-interest. Furthermore, the imaging device 42a may include an auto focus (AF) function and the distance to the region-of-interest may be calculated by focusing, by the imaging device 42a, on the position of the region-of-interest estimated by the region-of-interest estimation unit 22. The magnification can be set to high magnification when the distance to the region-of-interest is long, and can be set to low magnification when the distance to the region-of-interest is short, for example.

In this manner, according to the twelfth embodiment, the endoscope operator 5062 can easily set the magnification by selecting one zoom frame from the plurality of zoom frames 112c to 112f displayed on the display device 50.

Furthermore, according to the twelfth embodiment, the zoom processing unit 26 (magnified image generation unit) generates the magnified surgical field image L(x, y) at a magnification appropriate for the distance to the region-of-interest. Therefore, even when the endoscope 5001 moves in the anteroposterior direction with respect to the affected part, the affected part can be continuously observed with a constant size.

Thirteenth Embodiment

Figure 20:
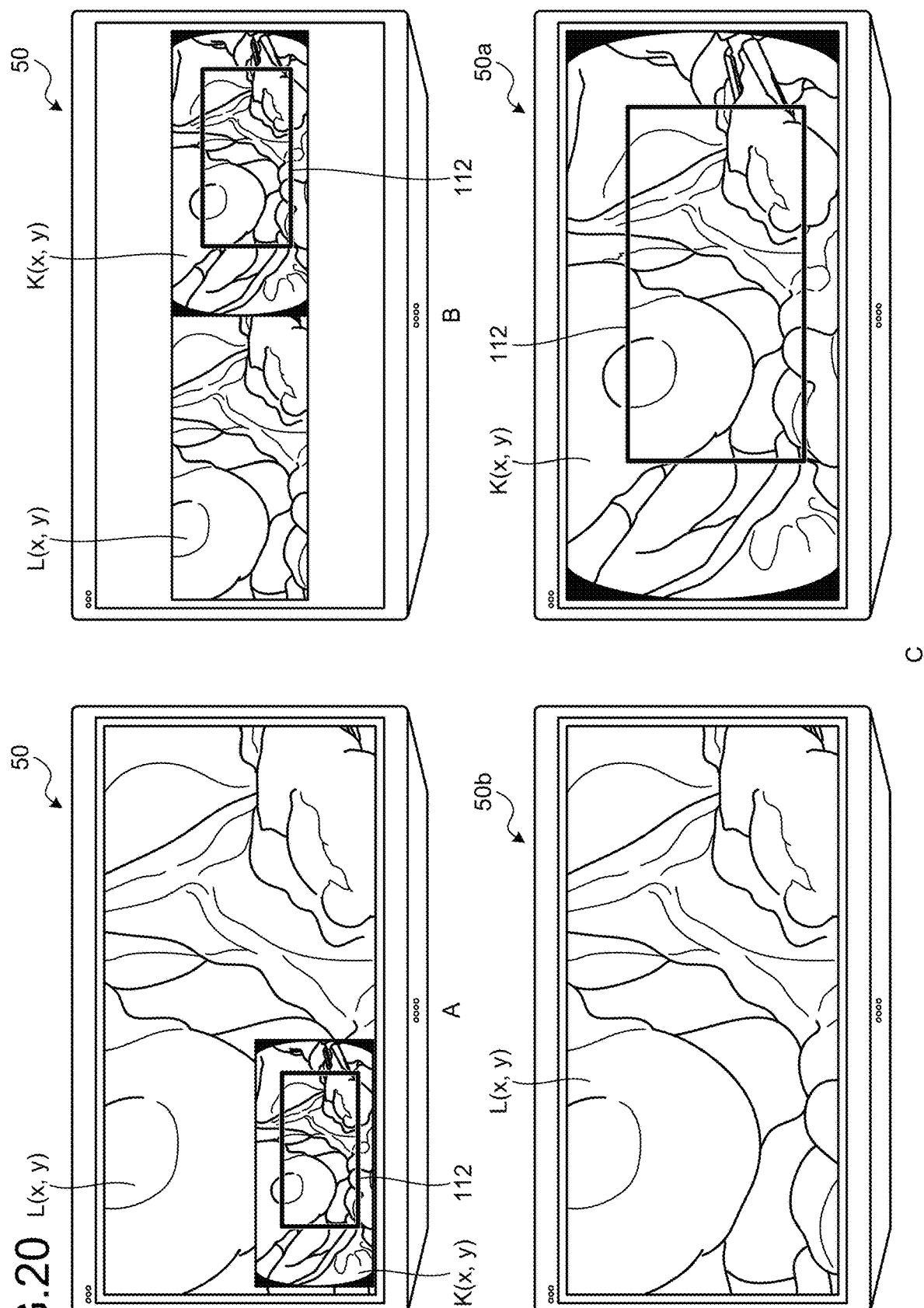
FIG. 20 is a view illustrating an example of a zoom frame display method when a medical observation system is applied.

FIG. 20 is a view illustrating an example of a method of displaying the zoom frame 112 when the medical observation system 10a is applied.

The zoom processing unit 26 may cause the display control unit 40 to display the zoom frame 112 to be superimposed on the surgical field image K(x, y) displayed on the display device 50.

FIG. 20A is an example in which the zoom frame 112 is displayed within the surgical field image K(x, y) displayed to be superimposed on a part of the magnified surgical field image L(x, y).

FIG. 20B is an example in which the zoom frame 112 is displayed within the surgical field image K(x, y) displayed adjacent to the magnified surgical field image L(x, y).

FIG. 20C is an example in which the zoom frame 112 is displayed within the surgical field image K(x, y) displayed on the display device 50a different from the display device 50b displaying the magnified surgical field image L(x, y).

In this manner, according to the thirteenth embodiment, the endoscope operator 5062 can easily confirm the position of the zoom frame 112. This enables the endoscope operator 5062 to predict the arrival of the zoom frame 112 at the screen edge, making it possible to prevent an occurrence of vignetting that occurs when the display range of the magnified surgical field image L(x, y) exceeds the edge of the surgical field image K(x, y).

Fourteenth Embodiment

In the medical observation system 10a described in the first embodiment, in order to improve the visibility of the surgical field image K(x, y) and the magnified surgical field image L(x, y) displayed on the display device 50, it is allowable to perform camera shake correction processing and exposure amount adjustment for these images. The camera shake correction processing is performed by the zoom processing unit 26 of FIG. 2, for example, and the exposure amount adjustment is performed by the development processing unit 18 of FIG. 2.

More specifically, the zoom processing unit 26 calculates the movement amount and movement direction of an object appearing in the image across a plurality of captured images, with respect to the surgical field image K(x, y) and the magnified surgical field image L(x, y). The captured image is electronically shifted in accordance with the calculated movement amount and movement direction, thereby generating an image in which camera shake has been corrected.

The magnified surgical field image L(x, y) is an observation image of a region narrower than the surgical field image K(x, y), and thus, has a larger amount of image blurring caused by camera shake. Therefore, it is desirable that the camera shake correction on the magnified surgical field image L(x, y) performed by the zoom processing unit 26 will have higher camera shake correction effects compared to the camera shake correction for the surgical field image K(x, y).

Furthermore, the development processing unit 18 may set a digital gain and a gamma curve separately for the surgical field image K(x, y) and the magnified surgical field image L(x, y), thereby individually adjusting the exposure amount.

In this manner, according to the fourteenth embodiment, the zoom processing unit 26 (magnified image generation unit) performs camera shake correction onto the surgical field image K(x, y) and the magnified surgical field image L(x, y). Therefore, even in a case where camera shake occurs in the surgical field image K(x, y) captured by the endoscope 5001, it is possible to obtain a surgical field image K(x, y) and a magnified surgical field image L(x, y) having high visibility due to camera shake correction.

Fifteenth Embodiment

Figure 21:
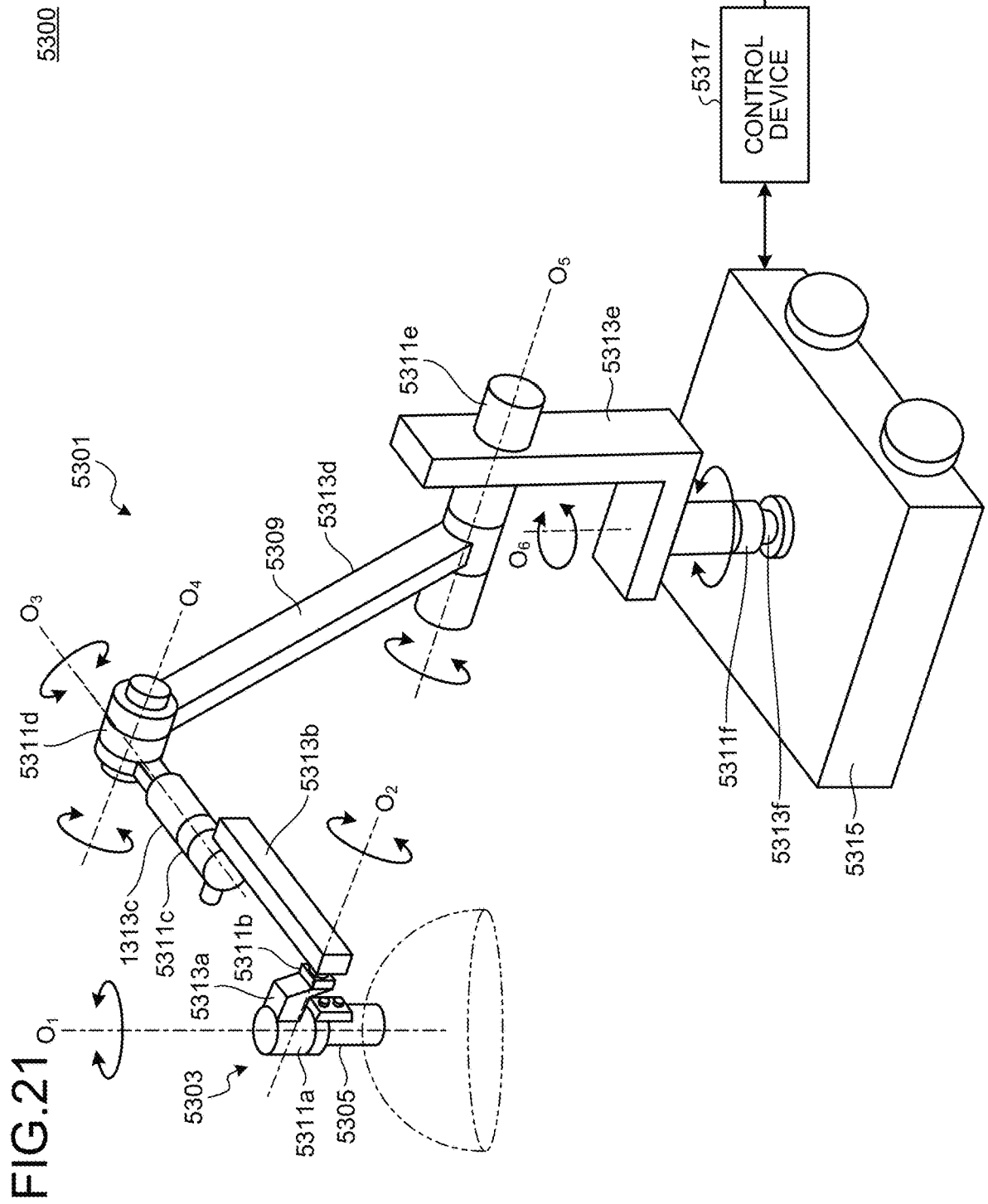
FIG. 21 is a view illustrating an example of a schematic configuration of a microscopic surgery system to which the techniques according to the present disclosure is applicable.

FIG. 21 is a view illustrating an example of a schematic configuration of a microscopic surgery system 5300 to which the techniques according to the present disclosure is applicable. Referring to FIG. 21, the microscopic surgery system 5300 includes a microscope device 5301, a control device 5317, and a display device 50. In the following description of the microscopic surgery system 5300, a "user" means a surgeon, an operator, an assistant, or any other medical staff who uses the microscopic surgery system 5300.

The microscope device 5301 includes a microscope unit 5303 for performing magnified observation of an observation target (patient's surgical site), an arm unit 5309 that supports, at its distal end, the microscope unit 5303, and a base unit 5315 that supports the proximal end of the arm unit 5309.

The microscope unit 5303 includes a tubular portion 5305 that has a substantially cylindrical shape, and an imaging unit (not illustrated) provided inside the tubular portion 5305. The microscope unit 5303 is an electronic imaging microscope unit (also referred to as a video microscope unit) that electronically captures an image using the imaging unit. The imaging unit is an example of an imaging device in the present disclosure.

On an aperture surface at the lower end of the tubular portion 5305, a cover glass slip is provided to protect the imaging unit inside. The light coming from the observation target (hereinafter, also referred to as observation light) passes through the cover glass slip and is incident on the imaging unit inside the tubular portion 5305. Note that a light source being a light emitting diode (LED) may be provided inside the tubular portion 5305, and light may be applied to the observation target from the light source through the cover glass slip, at the time of imaging.

The imaging unit includes: an optical system that collects observation light; and an imaging element that receives the observation light collected by the optical system. The optical system includes a combination of a plurality of lenses such as a zoom lens and a focus lens, and its optical characteristics are adjusted so that observation light is focused on a light receiving surface of the imaging element. The imaging element receives the observation light and photoelectrically converts the received light to generate a signal corresponding to the observation light, that is, an image signal corresponding to the observation image. An example of an applicable imaging element is a device capable of color imaging having a Bayer array. The imaging element may be various known imaging elements such as a CMOS image sensor or a CCD image sensor. The image signal generated by the imaging element is transmitted to the control device 5317 as RAW data. Here, the transmission of this image signal may be preferably performed by optical communication. This is because, at the surgical site, the surgeon performs surgery while observing the condition of the affected part using captured images, and thus displaying moving images of the surgical field in real time as much as possible is demanded for safer and more reliable surgery. By transmitting the image signal by optical communication, it is possible to display the captured image with low latency.

The imaging unit may include a drive mechanism that moves the zoom lens and the focus lens of the optical system along the optical axis. By appropriately moving the zoom lens and the focus lens by the drive mechanism, it is possible to adjust the magnification of the captured image and the focal length at the time of imaging. Furthermore, the imaging unit may be equipped with various functions that can be generally provided in an electronic imaging microscope unit, such as an auto exposure (AE) function and an AF function.

Furthermore, the imaging unit may be configured as a single-plate imaging unit having one imaging element, or may be configured as a multi-plate imaging unit having a plurality of imaging elements. When the imaging unit includes multiple plates, for example, each of imaging elements may generate an image signal corresponding to one color of RGB, and a color image may be obtained by combining these individual color image signals. Alternatively, the imaging unit may include a pair of imaging elements for acquiring image signals individually for the right eye and the left eye corresponding to stereoscopic vision (3D display). The 3D display enables the surgeon to grasp the depth of the living tissue more accurately in the surgical field. When the imaging unit includes multiple plates, a plurality of optical systems may be provided corresponding to each of the imaging elements.

The arm unit 5309 has a configuration in which a plurality of links (first link 5313*a* to sixth link 5313*f*) is swivelably coupled to each other via a plurality of joints (first joint 5311*a* to sixth joint 5311*f*).

The first joint 5311*a* has a substantially columnar shape, and swivelably supports, at its distal end (lower end), an upper end of the tubular portion 5305 of the microscope unit 5303 about a rotation axis (first axis $O_1$) parallel to the central axis of the tubular portion 5305. Here, the first joint 5311*a* can be configured such that the first axis $O_1$ is aligned with the optical axis of the imaging unit of the microscope unit 5303. With this configuration, swivel movement of the microscope unit 5303 about the first axis $O_1$ will make it possible to change the field of view so as to rotate the captured image.

The first link 5313*a* fixedly supports the first joint 5311*a* at the distal end. Specifically, the first link 5313*a* is a rod-shaped member having a substantially L-shape. Having one side of the distal end side extending in a direction orthogonal to the first axis $O_1$, the first link 5313*a* is connected to the first joint 5311*a* with an end of the one side being in contact with an upper end of an outer circumference of the first joint 5311*a*. The second joint 5311*b* is connected to the end of the other side on the proximal end side of the substantially L-shape of the first link 5313*a*.

The second joint 5311*b* has a substantially columnar shape, and swivelably supports, at its distal end, the proximal end of the first link 5313*a* about a rotation axis (second axis $O_2$) orthogonal to the first axis $O_1$. The distal end of the second link 5313*b* is fixedly connected to the proximal end of the second joint 5311*b*.

The second link 5313*b* is a rod-shaped member having a substantially L-shape. Having one side of the distal end side extending in a direction orthogonal to the second axis $O_2$, the second link 5313*b* has an end of the one side fixedly connected to the proximal end of the second joint 5311*b*. The third joint 5311*c* is connected to the other side of the proximal end side of the substantially L-shape of the second link 5313*b*.

The third joint 5311*c* has a substantially columnar shape, and swivelably supports, at its distal end, the proximal end of the second link 5313*b* about a rotation axis (third axis $O_3$) orthogonal to the first axis $O_1$ and the second axis $O_2$. The distal end of the third link 5313*c* is fixedly connected to the proximal end of the third joint 5311*c*. With the swivel movement of the configuration on the distal end side including the microscope unit 5303 about the second axis $O_2$ and the third axis $O_3$, it is possible to move the microscope unit 5303 so as to change the position of the microscope unit 5303 in a horizontal plane. That is, by controlling the rotation around the second axis $O_2$ and the third axis $O_3$, the field of view of the captured image can be moved in a plane.

The third link 5313*c* is configured so that its distal end side has a substantially columnar shape, and the proximal end of the third joint 5311*c* is fixedly connected to the distal end of the columnar shape so as to have a substantially same central axis. The proximal end side of the third link 5313*c* has a prismatic shape, with its end being connected to the fourth joint 5311*d*.

The fourth joint 5311*d* has a substantially columnar shape, and swivelably supports, at its distal end, the proximal end of the third link 5313*c* about a rotation axis (fourth axis $O_4$) orthogonal to the third axis $O_3$. The distal end of the fourth link 5313*d* is fixedly connected to the proximal end of the fourth joint 5311*d*.

The fourth link 5313*d* is a rod-shaped member that extends substantially linearly. Extending so as to be orthogonal to the fourth axis $O_4$, the fourth link 5313*d* is fixedly connected to the fourth joint 5311*d* so as to bring an end of the distal end in contact with a substantially columnar side surface of the fourth joint 5311*d*. The fifth joint 5311*e* is connected to the proximal end of the fourth link 5313*d*.

The fifth joint 5311*e* has a substantially columnar shape, and swivelably supports, at its distal end, the proximal end of the fourth link 5313*d* about a rotation axis (fifth axis $O_5$) parallel to the fourth axis $O_4$. The distal end of the fifth link 5313*e* is fixedly connected to the proximal end of the fifth joint 5311*e*. The fourth axis $O_4$ and the fifth axis $O_5$ are rotation axes that allows movement of the microscope unit 5303 in the up-down direction. With a swivel movement of the configuration on the distal end side including the microscope unit 5303 about the fourth axis $O_4$ and the fifth axis $O_5$, it is possible to adjust height of the microscope unit 5303, that is, the distance between the microscope unit 5303 and the observation target.

The fifth link 5313*e* has a configuration including a combination of a first member having a substantially L-shape and having one side extending in the vertical direction and the other side extending in the horizontal direction, and a rod-shaped second member and extending vertically downward from a portion of the first member extending in the horizontal direction. The proximal end of the fifth joint 5311e is fixedly connected to the vicinity of the upper end of the portion extending in the vertical direction of the first member of the fifth link 5313e. The sixth joint 5311f is connected to the proximal end (lower end) of the second member of the fifth link 5313e.

The sixth joint 5311f has a substantially columnar shape, and swivelably supports, at its distal end, the proximal end of the fifth link 5313e about a rotation axis (sixth axis $O_6$) parallel to the vertical direction. The distal end of the sixth link 5313f is fixedly connected to the proximal end of the sixth joint 5311f.

The sixth link 5313f is a rod-shaped member extending in the vertical direction, with a proximal end of which being fixedly connected to the upper surface of the base unit 5315.

The rotatable ranges of the first joint 5311a to the sixth joint 5311f are appropriately set so as to enable a desired movement of the microscope unit 5303. With this setting, the arm unit 5309 having the configuration described above can achieve a movement of six degrees of freedom, namely, three degrees of freedom of translation and three degrees of freedom of rotation regarding the movement of the microscope unit 5303. In this manner, with the configuration of the arm unit 5309 that achieves six degrees of freedom regarding the movement of the microscope unit 5303, it is possible to freely control the position and orientation of the microscope unit 5303 within a movable range of the arm unit 5309. This makes it possible to observe the surgical field from any angle, enabling execution of the surgery further smoothly.

The configuration of the arm unit 5309 illustrated in the figure is only an example, and the number and shape (length) of the links constituting the arm unit 5309, the number of joints, the arrangement position, the direction of the rotation axis, or the like, may be appropriately designed so that the desired degree of freedom can be achieved. For example, as described above, in order to freely move the microscope unit 5303, the arm unit 5309 is preferably configured to have six degrees of freedom. However, the arm unit 5309 may be configured to have more degrees of freedom (namely, a redundant degree of freedom). In a case where the redundant degree of freedom exists, it is possible, in the arm unit 5309, to change the orientation of the arm unit 5309 while the position and orientation of the microscope unit 5303 are fixed. This makes it possible to achieve more convenient control for the surgeon, including controlling the orientation of the arm unit 5309 so as to prevent the arm unit 5309 from interfering with the field of view of the surgeon viewing the display device 50.

Here, the first joint 5311a to the sixth joint 5311f can include an actuator equipped with a drive mechanism such as a motor, and an encoder to detect a rotation angle at each of the joints, or the like. With appropriate control of the drive of individual actuators provided in the first joint 5311a to the sixth joint 5311f by the control device 5317, it is possible to control the orientation of the arm unit 5309, that is, the position and orientation of the microscope unit 5303. Specifically, the control device 5317 can grasp the current orientation of the arm unit 5309 and the current position and orientation of the microscope unit 5303 based on the information regarding the rotation angle of each of joints detected by the encoder. Using the grasped information, the control device 5317 calculates control values (for example, rotation angle or generated torque) for each of joints so that the microscope unit 5303 achieves a desired movement, and drives the drive mechanism of each of joints based on the control values. At this time, the method for controlling the arm unit 5309 by the control device 5317 is not limited, and various known control methods such as force control or position control may be applied.

For example, it is also allowable to have a configuration in which the surgeon appropriately performs operation input through an input device (not illustrated), and the control device 5317 appropriately controls the drive of the arm unit 5309 based on the operation input, so as to control the position and orientation of the microscope unit 5303. With this control, it is possible to move the microscope unit 5303 from a certain position to another certain position, and then fixedly support the unit at the new position after the movement. In consideration of the convenience for the surgeon, it is preferable to use an input device such as a foot switch that can be operated even when the surgeon is holding the surgical tool by hand. Furthermore, the operation input may be performed in a non-contact operation based on a gesture detection or line-of-sight detection using a wearable device or a camera provided in the operating room. As a result of this, even a user located in a clean region can operate the device located in an unclean region with a higher degree of freedom. Alternatively, the arm unit 5309 may be operated by a master-slave method. In this case, the arm unit 5309 can be remotely controlled by the user via an input device installed at a location away from the operating room.

Furthermore, in a case where force control is applied, it is also allowable to use a power assist control in which the actuators of the first joint 5311a to the sixth joint 5311f are driven so as to achieve smooth movement of the arm unit 5309 in response to an external force received from the user. With this control, when the user grips the microscope unit 5303 and tries to move its position directly, the microscope unit 5303 can be moved with a relatively light force. This makes it possible to move the microscope unit 5303 more intuitively and with a simpler operation, improving user convenience.

Furthermore, the drive of the arm unit 5309 may be controlled so as to perform a pivot operation. Here, the pivot operation is an operation of moving the microscope unit 5303 so that the optical axis of the microscope unit 5303 constantly faces a predetermined point in space (hereinafter, referred to as a pivot point). With the pivot operation, it is possible to observe an identical observation position from various directions, enabling observation of the affected part in more detail. In a case where focal length adjustment is disabled in the microscope unit 5303, it is preferable to perform the pivot operation with a fixed distance between the microscope unit 5303 and the pivot point. In this case, the distance between the microscope unit 5303 and the pivot point is only required to be adjusted to a fixed focal length of the microscope unit 5303. With this configuration, the microscope unit 5303 will move on a hemisphere (schematically illustrated in FIG. 21) having a radius corresponding to the focal length centered on the pivot point, leading to acquisition of a clear image even when the observation direction is changed. In contrast, in a case where focal length adjustment is enabled in the microscope unit 5303, it is allowable to perform the pivot operation with a variable distance between the microscope unit 5303 and the pivot point. In this case, for example, it is allowable to have a configuration in which the control device 5317 calculates the distance between the microscope unit 5303 and the pivot point based on the information regarding the rotation angle of individual joints detected by the encoder, and automatically adjusts the focal length of the microscope unit 5303 based on the calculation result. Alternatively, in a case where the microscope unit 5303 includes an AF function, the focal length may be automatically adjusted by the AF function each time the distance between the microscope unit 5303 and the pivot point changes due to the pivot operation.

By controlling the operations of the microscope device 5301 and the display device 50, the control device 5317 comprehensively controls the operation of the microscopic surgery system 5300. For example, by controlling to operate the actuators of the first joint 5311*a* to the sixth joint 5311*f* with a predetermined control method, the control device 5317 controls the drive of the arm unit 5309. Furthermore, for example, by controlling the operation of the brakes of the first joint 5311*a* to the sixth joint 5311*f*, the control device 5317 changes the operation mode of the arm unit 5309. Furthermore, the control device 5317 has the function of the camera control unit 12*a* described in the first embodiment. In addition, from within the surgical field image K(x, y) captured by the imaging unit of the microscope unit 5303, the control device 5317 generates the magnified surgical field image L(x, y) in which the region-of-interest is magnified and controls to display the generated image on the display device 50. The control device 5317 may perform various known signal processing procedures such as development processing (demosaic processing) and image quality improvement processing (band enhancement processing, super-resolution processing, noise reduction (NR) processing, and/or camera shake correction processing) on the surgical field image K(x, y) acquired by the imaging unit of the microscope unit 5303 in the microscope device 5301.

The communication between the control device 5317 and the microscope unit 5303 and the communication between the control device 5317 and the first joint 5311*a* to the sixth joint 5311*f* may be wired communication or wireless communication. In the case of wired communication, the communication may be electric signal communication, or optical communication. In this case, the transmission cable used for wired communication can be configured as an electric signal cable, an optical fiber, or a composite cable thereof depending on the communication method. In contrast, in the case of wireless communication, there is no need to install a transmission cable in the operating room, making it possible to suppress the situation in which the transmission cable hinders movement of the medical staff in the operating room.

The control device 5317 may be a processor such as a central processing unit (CPU) or a graphics processing unit (GPU), or a microcomputer or a control board including both the processor and storage elements such as memory. The various functions described above can be actualized by operation of the processor of the control device 5317 based on a predetermined program. In the illustrated example, the control device 5317 is provided as a separate device from the microscope device 5301. However, the control device 5317 may be installed inside the base unit 5315 of the microscope device 5301 so as to be integrated with the microscope device 5301. Alternatively, the control device 5317 may be composed of a plurality of devices. For example, it is also allowable to have a configuration in which a microcomputer and a control board are arranged individually in the microscope unit 5303 and the first joint 5311*a* to the sixth joint 5311*f* of the arm unit 5309, having communicable connection to each other, thereby achieving functionality similar to the control device 5317.

The display device 50 is provided in the operating room and displays an image corresponding to the image data generated by the control device 5317 under the control of the control device 5317. That is, at least the magnified surgical field image L(x, y), out of the surgical field image K(x, y) and the magnified surgical field image L(x, y) captured by the microscope unit 5303, is displayed on the display device 50. Note that, in place of the surgical field image K(x, y) or together with the surgical field image K(x, y), the display device 50 may display various types of surgical information such as physical information of the patient and information regarding the surgical procedure. In this case, the display of the display device 50 may be appropriately switched by an operation by the user. Alternatively, the display device 50 may be provided in plurality and each of the plurality of display devices 50 may display the surgical field image K(x, y), the magnified surgical field image L(x, y), and various type of information related to surgery. The display device 50 may be provided as various known display devices such as a liquid crystal display device or an EL display device.

Figure 22:
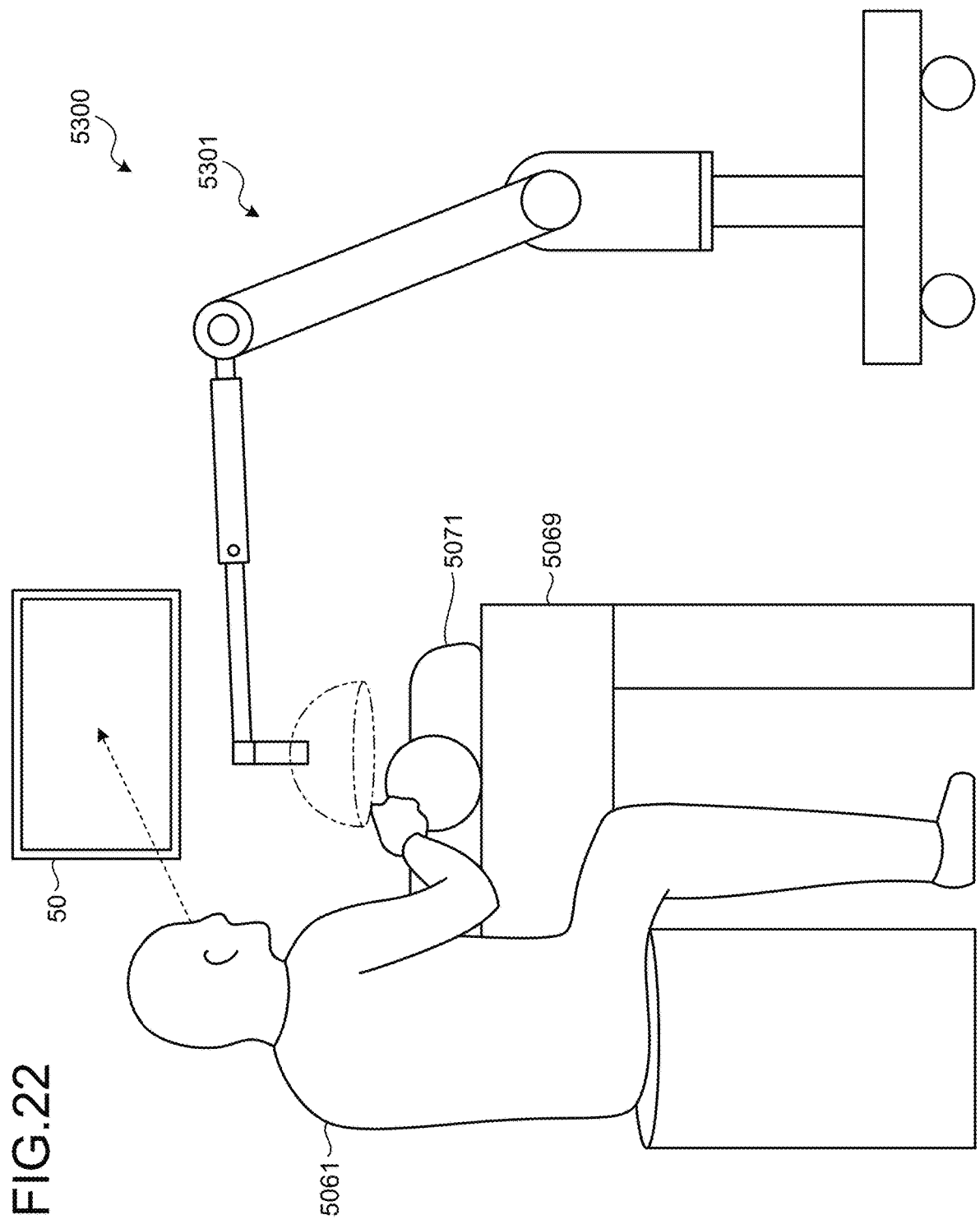
FIG. 22 is a view illustrating a scene of surgery using a microscopic surgery system.

FIG. 22 is a diagram illustrating a scene of surgery using the microscopic surgery system 5300 illustrated in FIG. 21. FIG. 22 schematically illustrates a scene in which the surgeon 5061 is during surgery on a patient 5071 on a patient bed 5069 using the microscopic surgery system 5300. For the sake of simplicity, FIG. 22 omits illustration of the control device 5317 out of the configuration of the microscopic surgery system 5300, and simplifies illustration of the microscope device 5301 including the microscope unit 5303 (FIG. 21).

As illustrated in FIG. 22, at the time of surgery, at least the magnified surgical field image L(x, y), out of the surgical field image L(x, y) and the magnified surgical field image L(x, y) captured by the microscope device 5301, will be displayed using the microscopic surgery system 5300 as magnified images on the display device 50 installed on the wall surface of the operating room. The display device 50 is installed at a position facing the surgeon 5061. The surgeon 5061 performs various types of procedures such as resecting the affected part, or the like, while observing the state of the surgical site by viewing the image projected on the display device 50.

Figure 23:
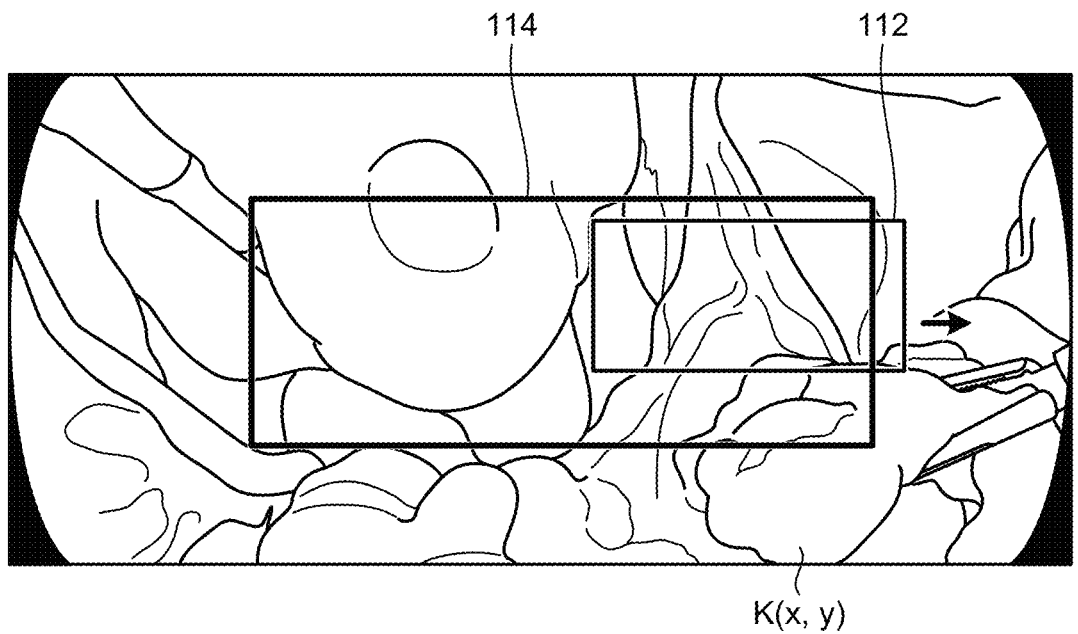
FIG. 23 is a view illustrating an example of a control state in which a zoom frame is held in a central portion of a screen provided in a microscopic surgery system.

FIG. 23 is a view illustrating an example of a control state in which a zoom frame 112 is held in a central portion of a screen provided in the microscopic surgery system 5300.

The control device 5317 constantly monitors the position of the zoom frame 112 in the surgical field image K(x, y). Specifically, the control device 5317 constantly monitors whether the zoom frame 112 extends outside a control determination frame 114 set at the substantially central portion of the surgical field image K(x, y).

When it is detected that the zoom frame 112 extends outside the control determination frame 114, the control device 5317 controls angles of the first joints 5311*a* to the sixth joint 5311*f* so that the zoom frame 112 stays inside the control determination frame 114, thereby controlling the position and orientation of the microscope unit 5303.

In the example of FIG. 23, the zoom frame 112 extends outside on the right side of the control determination frame 114. In this case, the control device 5317 controls the position and orientation of the microscope unit 5303 so that the zoom frame 112 stays inside the control determination frame 114. That is, in the example of FIG. 23, the control device 5317 moves the position and orientation of the microscope unit 5303 to the right and thereby keeps the zoom frame 112 inside the control determination frame 114. In cases where the zoom frame 112 extends outside the control determination frame 114 in a direction other than the right side, the control device 5317 controls the position and orientation of the microscope unit 5303 so that the zoom frame 112 stays inside the control determination frame 114 in a similar manner.

In this manner, according to the fifteenth embodiment, the control device 5317 controls the position and orientation of the microscope unit 5303 so that the zoom frame 112 stays inside the control determination frame 114. Therefore, when the surgeon 5061 performs the surgery alone, the surgeon 5061 would not need to hold the microscope unit 5303 and can concentrate on the surgery. The control of the position and orientation of the microscope unit 5303 described in the fifteenth embodiment is also applicable to the medical observation system 10a described in the first embodiment, for example. That is, in the medical observation system 10a, the position and orientation of the endoscope 5001 can be controlled so that the zoom frame 112 constantly stays at a predetermined position of the display device 50.

Furthermore, according to the fifteenth embodiment, the imaging unit is mounted on the microscope unit 5303. Therefore, when performing surgery using a microscope, or the like, the surgeon 5061 can stably observe the affected part in a magnified state.

An example of the microscopic surgery system 5300 to which the technique according to the present disclosure can be applied has been described above. Although the microscopic surgery system 5300 has been described here as an example, the system to which the technique according to the present disclosure can be applied is not limited to such an example. For example, the microscope device 5301 can also function as a support arm device that supports, at its distal end, other observation devices or other surgical tools, instead of the microscope unit 5303. An example of the other applicable observation devices is an endoscope. Furthermore, examples of the other applicable surgical tools include forceps, tweezers, an insufflation tube for insufflation, or energy treatment tools for tissue incision or blood vessel sealing using ablation, or the like. By supporting these observation devices and surgical tools with a support arm device, it is possible to fix the position of the devices or tools more stably and reduce the burden on the medical staff as compared with the case where the medical staff grasps them manually. The technique according to the present disclosure may be applied to such a support arm device that supports a configuration other than a microscope unit.

The effects described in the present specification are merely examples, and thus, there may be other effects, not limited to the exemplified effects.

Furthermore, the embodiment of the present disclosure is not limited to the above-described embodiment, and various modifications can be made without departing from the scope and spirit of the present disclosure.

The present disclosure may have the following configurations.

(1)

A medical observation system comprising:
an imaging device that images a surgical field and obtains a surgical field image;
a three-dimensional information generation unit that generates three-dimensional information of the surgical field from the surgical field image captured by the imaging device;
a setting unit that sets at least one region-of-interest based on at least one the surgical field image captured at a predetermined timing by the imaging device;
an estimation unit that estimates an existence position of the region-of-interest from within a surgical field image captured at a timing different from the predetermined timing based on the three-dimensional information and the position of the region-of-interest set by the setting unit;
a magnified image generation unit that generates a magnified surgical field image in which the estimated region-of-interest is magnified at a predetermined magnification; and
a display control unit that outputs at least the magnified surgical field image.

(2)

The medical observation system according to (1), wherein the display control unit controls to display the surgical field image and the magnified surgical field image.

(3)

The medical observation system according to (2), wherein the display control unit controls to display the surgical field image and the magnified surgical field image adjacent to each other on one display device.

(4)

The medical observation system according to (2), wherein the display control unit controls to display the surgical field image so as to be superimposed on a part of the magnified surgical field image, on one display device.

(5)

The medical observation system according to (2), wherein the display control unit controls to display the surgical field image and the magnified surgical field image individually on two display devices.

(6)

The medical observation system according to any one of (1) to (5),
wherein the setting unit designates a specific position of the surgical field image displayed by the display control unit, as a region-of-interest, in a state where the specific position is aligned with a predetermined position and on condition that a setting signal instructing the setting of the region-of-interest has occurred.

(7)

The medical observation system according to any one of (1) to (5),
wherein the setting unit sets a region-of-interest at a position instructed by an input device in the surgical field image displayed by the display control unit.

(8)

The medical observation system according to any one of (1) to (7),
wherein, in a case where the region-of-interest has reached an edge of the surgical field image, or comes to a position to overlap a vignetting region of the surgical field image, the magnified image generation unit generates a
magnified surgical field image that stores a predetermined pixel value in a region beyond the edge and the region overlapping the vignetting region in the region-of-interest.

(9)

The medical observation system according to any one of (1) to (7),
wherein, in a case where the region-of-interest has reached the edge of the surgical field image,
the magnified image generation unit generates a magnified surgical field image in which an edge of the magnified surgical field image is aligned with an edge of the surgical field image.

(10)

The medical observation system according to any one of (1) to (7), wherein, in a case where the region-of-interest has reached an edge of the surgical field image, or comes to a position to overlap a vignetting region of the surgical field image, the magnified image generation unit stops generation of a magnified surgical field image.

(11)

The medical observation system according to any one of (1) to (10), wherein the imaging device includes one imaging element, and the three-dimensional information generation unit generates three-dimensional information of a surgical field based on at least two surgical field images captured by the imaging device at different times.

(12)

The medical observation system according to any one of (1) to (10), wherein the imaging device includes two imaging elements that image different ranges partially overlapping each other, and the three-dimensional information generation unit generates three-dimensional information of a surgical field based on two surgical field images captured by the imaging elements at a same time.

(13)

The medical observation system according to any one of (1) to (10), wherein the imaging device includes one imaging element and a distance measuring device that measures a distance to an object, and the three-dimensional information generation unit generates three-dimensional information of a surgical field based on the surgical field image captured by the imaging element and the distance measured by the distance measuring device.

(14)

The medical observation system according to any one of (1) to (13), wherein the setting unit further includes a function of designating a distance range containing the region-of-interest, and sets the region-of-interest within the designated distance range.

(15)

The medical observation system according to any one of (1) to (14), wherein the magnified image generation unit generates the magnified surgical field image at a magnification corresponding to the distance to the region-of-interest.

(16)

The medical observation system according to any one of (1) to (15), wherein the magnified image generation unit performs camera shake correction on the surgical field image and the magnified surgical field image.

(17)

The medical observation system according to any one of (1) to (16), wherein the imaging device is mounted on an endoscope.

(18)

The medical observation system according to any one of (1) to (16), wherein the imaging device is mounted on a microscope.

(19)

A medical observation apparatus comprising:

a three-dimensional information generation unit that generates three-dimensional information of a surgical field from a surgical field image obtained by imaging the surgical field;

a setting unit that sets at least one region-of-interest based on at least one the surgical field image captured at a predetermined timing;

an estimation unit that estimates an existence position of the region-of-interest from within a surgical field image captured at a timing different from the predetermined timing, based on the three-dimensional information and the position of the region-of-interest set by the setting unit;

a magnified image generation unit that generates a magnified surgical field image in which the estimated region-of-interest is magnified at a predetermined magnification; and a display control unit that outputs at least the magnified surgical field image.

(20)

A medical observation method comprising:

a step of generating three-dimensional information of a surgical field from a surgical field image obtained by imaging the surgical field;

a step of setting at least one region-of-interest based on at least one the surgical field image captured at a predetermined timing;

a step of estimating an existence position of the region-of-interest from within a surgical field image captured at a timing different from the predetermined timing, based on the three-dimensional information and the position of the region-of-interest;

a step of generating a magnified surgical field image in which the estimated region-of-interest is magnified at a predetermined magnification; and a step of outputting at least the magnified surgical field image.

REFERENCE SIGNS LIST 10a, 10b, 10c, 10d, 10e, 10f MEDICAL OBSERVATION SYSTEM
12a, 12b, 12c CAMERA CONTROL UNIT (MEDICAL OBSERVATION APPARATUS)
14 THREE-DIMENSIONAL INFORMATION GENERATION UNIT
15 MAP GENERATION UNIT
16 SELF-POSITION ESTIMATION UNIT
18 DEVELOPMENT PROCESSING UNIT
20 REGION-OF-INTEREST SETTING UNIT (SETTING UNIT)
22 REGION-OF-INTEREST ESTIMATION UNIT (ESTIMATION UNIT)
24 THREE-DIMENSIONAL MAP DATA STORAGE UNIT
26 ZOOM PROCESSING UNIT (MAGNIFIED IMAGE GENERATION UNIT)
40 DISPLAY CONTROL UNIT
42a, 42b, 42c, 42d IMAGING DEVICE
44a, 44b, 44c, 44d IMAGING ELEMENT
46 IMAGE PLANE PHASE DIFFERENCE SENSOR
48 DEPTH SENSOR (DISTANCE MEASURING DEVICE)
50, 50a, 50b DISPLAY DEVICE
52a FIRST DISPLAY REGION

52b SECOND DISPLAY REGION
110 REGION-OF-INTEREST FRAME
112, 112a, 112b ZOOM FRAME
5001 ENDOSCOPE
5061 SURGEON
5062 ENDOSCOPE OPERATOR
5063 ASSISTANT
5300 MICROSCOPIC SURGERY SYSTEM
5303 MICROSCOPE UNIT
5317 CONTROL DEVICE
D(X, Y, Z) THREE-DIMENSIONAL MAP (THREE-DIMENSIONAL INFORMATION)
K(x, y), K(x, y, t) SURGICAL FIELD IMAGE
L(x, y) MAGNIFIED SURGICAL FIELD IMAGE

The invention claimed is:

1. A medical observation system comprising:
an imaging device that images a surgical field and obtains a surgical field image; and
circuitry configured to:
generate three-dimensional information of the surgical field from the surgical field image captured by the imaging device;
set at least one region-of-interest based on at least one of the surgical field image captured at a predetermined timing by the imaging device;
estimate an existence position of the region-of-interest from within a surgical field image captured at a timing different from the predetermined timing based on the three-dimensional information and the position of the region-of-interest set;
generate a magnified surgical field image in which the estimated region-of-interest is magnified at a predetermined magnification; and
output at least the magnified surgical field image to a display,
wherein, in a case where the region-of-interest has reached an edge of the surgical field image or overlaps a vignetting region of the surgical field image, the circuitry is to:
generate a magnified surgical field image that stores a predetermined pixel value in a region beyond the edge and the region overlapping the vignetting region in the region-of-interest,
generate a magnified surgical field image in which an edge of the magnified surgical field image is aligned with an edge of the surgical field image, or
stop generation of a magnified surgical field image.

2. The medical observation system according to claim 1, wherein the circuitry is configured to output the surgical field image and the magnified surgical field image to the display.

3. The medical observation system according to claim 2, wherein the circuitry is configured to control the display to display the surgical field image and the magnified surgical field image adjacent to each other.

4. The medical observation system according to claim 2, wherein circuitry is configured to control the display to the display the surgical field image superimposed on a part of the magnified surgical field image.

5. The medical observation system according to claim 2, wherein the display includes two separate display panels, and the circuitry is configured to control the display to display the surgical field image on a first display panel and to display the magnified surgical field image individually on a second display panel.

6. The medical observation system according to claim 1, wherein the circuitry is configured to designate a specific position of the surgical field image to be displayed on the display, as a region-of-interest, in a state where the specific position is aligned with a predetermined position and on condition that a setting signal instructing the setting of the region-of-interest has occurred.

7. The medical observation system according to claim 1, wherein the circuitry is configured to set a region-of-interest at a position instructed by an input device in the surgical field image displayed on the display.

8. The medical observation system according to claim 1, wherein the imaging device includes one imaging element, and
the circuitry is configured to generate three-dimensional information of a surgical field based on at least two surgical field images captured by the imaging device at different times.

9. The medical observation system according to claim 1, wherein the imaging device includes two imaging elements that image different ranges partially overlapping each other, and
the circuitry is configured to generate three-dimensional information of a surgical field based on two surgical field images captured by the imaging elements at a same time.

10. The medical observation system according to claim 1, wherein the imaging device includes one imaging element and a distance measuring device that measures a distance to an object, and
the circuitry is configured to generate three-dimensional information of a surgical field based on the surgical field image captured by the imaging element and the distance measured by the distance measuring device.

11. The medical observation system according to claim 1, wherein the circuitry is configured to designate a distance range containing the region-of-interest, and set the region-of-interest within the designated distance range.

12. The medical observation system according to claim 1, wherein the circuitry is configured to generate the magnified surgical field image at a magnification corresponding to a distance to the region-of-interest.

13. The medical observation system according to claim 1 wherein the circuitry is configured to perform camera shake correction on the surgical field image and the magnified surgical field image.

14. The medical observation system according to claim 1, wherein the imaging device is mounted on an endoscope.

15. The medical observation system according to claim 1, wherein the imaging device is mounted on a microscope.

16. A medical observation apparatus comprising:
circuitry configured to:
generate three-dimensional information of the surgical field from the surgical field image captured by an imaging device;
set at least one region-of-interest based on at least one of the surgical field image captured at a predetermined timing by the imaging device;
estimate an existence position of the region-of-interest from within a surgical field image captured at a timing different from the predetermined timing based on the three-dimensional information and the position of the region-of-interest set;
generate a magnified surgical field image in which the estimated region-of-interest is magnified at a predetermined magnification; and output at least the magnified surgical field image to a display, wherein, in a case where the region-of-interest has reached an edge of the surgical field image or overlaps a vignetting region of the surgical field image, the circuitry is to:

generate a magnified surgical field image that stores a predetermined pixel value in a region be and the edge and the region overlapping the vignetting region in the region-of-interest, generate a magnified surgical field image in which an edge of the magnified surgical field image is aligned with an edge of the surgical field image, or stop generation of a magnified surgical field image.

17. A medical observation method comprising:

generating three-dimensional information of a surgical field from a surgical field image obtained by imaging the surgical field;

setting at least one region-of-interest based on at least one the surgical field image captured at a predetermined timing;

estimating an existence position of the region-of-interest from within a surgical field image captured at a timing different from the predetermined timing, based on the three-dimensional information and the position of the region-of-interest;

generating a magnified surgical field image in which the estimated region-of-interest is magnified at a predetermined magnification;

outputting at least the magnified surgical field image to a display; and determining whether the region-of-interest has reached an edge of the surgical field image, or comes to a position to overlap a vignetting region of the surgical field image;

in response to determination that the region-of-interest has reached the edge of the surgical field image or overlaps the vignetting region of the surgical field image, perform one of the following processes, generating a magnified surgical field image that stores a predetermined pixel value in a region beyond the edge and the region overlapping the vignetting region in the region-of-interest, generating a magnified surgical field image in which an edge of the magnified surgical field image is aligned with an edge of the surgical field image, or stopping generating of a magnified surgical field image.

18. The medical observation apparatus according to claim 16, wherein, in the case where the region-of-interest has reached the edge of the surgical field image or overlaps the vignetting region of the surgical field image, the circuitry is to generate a magnified surgical field image that stores a predetermined pixel value in a region beyond the edge and the region overlapping the vignetting region in the region-of-interest.

19. The medical observation apparatus according to claim 16, wherein in the case where the region-of-interest has reached the edge of the surgical field image or overlaps the vignetting region of the surgical field image, the circuitry is to generate a magnified surgical field image in which an edge of the magnified surgical field image is aligned with an edge of the surgical field image.

20. The medical observation apparatus according to claim 16, wherein in the case where the region-of-interest has reached the edge of the surgical field image or overlaps the vignetting region of the surgical field image, the circuitry is to stop generation of a magnified surgical field image.

* * * * *